(12) United States Patent
Sawada et al.

(10) Patent No.: US 9,256,068 B2
(45) Date of Patent: Feb. 9, 2016

(54) SPHERICAL ABERRATION CORRECTOR, METHOD OF SPHERICAL ABERRATION CORRECTION, AND CHARGED PARTICLE BEAM INSTRUMENT

(71) Applicant: JEOL Ltd., Tokyo (JP)

(72) Inventors: Hidetaka Sawada, Tokyo (JP); Yu Jimbo, Tokyo (JP)

(73) Assignee: JEOL Ltd., Tokyo (JP)

( * ) Notice: Subject to any disclaimer, the term of this patent is extended or adjusted under 35 U.S.C. 154(b) by 8 days.

(21) Appl. No.: 14/338,542

(22) Filed: Jul. 23, 2014

(65) Prior Publication Data
US 2015/0029593 A1    Jan. 29, 2015

(30) Foreign Application Priority Data
Jul. 24, 2013 (JP) .................................. 2013-153367

(51) Int. Cl.
*G02B 27/14* (2006.01)
*H01J 3/14* (2006.01)
(Continued)

(52) U.S. Cl.
CPC ............ *G02B 27/0037* (2013.01); *G01N 23/20* (2013.01); *G21K 1/08* (2013.01); *H01J 3/12* (2013.01); *H01J 3/26* (2013.01); *H01J 37/05* (2013.01); *H01J 37/147* (2013.01); *H01J 37/1472* (2013.01); *H01J 37/153* (2013.01); *H01J 37/28* (2013.01); *G02B 27/42* (2013.01); *G02B 27/4205* (2013.01); *H01J 3/04* (2013.01); *H01J 2237/1532* (2013.01); *H01J 2237/1534* (2013.01)

(58) Field of Classification Search
CPC .... G02B 27/0037; G02B 27/14; G02B 27/42; G02B 27/4205; H01J 3/02; H01J 3/04; H01J 3/023; H01J 3/025; H01J 3/12; H01J 3/14; H01J 3/26; H01J 37/05; H01J 37/147; H01J 37/1472; H01J 37/1478; H01J 37/153; H01J 37/26; H01J 37/28; H01J 2237/1532; H01J 2237/1534
USPC .......................... 359/637, 388, 558, 646, 672; 250/252.1, 306, 307, 309–311, 398, 250/396 ML, 396 R, 492.22, 492.3
See application file for complete search history.

(56) References Cited

U.S. PATENT DOCUMENTS

| 5,793,048 A | * | 8/1998 | Petric | ..................... B82Y 10/00 250/396 ML |
| 5,838,011 A | * | 11/1998 | Krijn | ..................... H01J 37/153 350/396 R |

(Continued)

FOREIGN PATENT DOCUMENTS

JP           201330278 A      2/2013

OTHER PUBLICATIONS

Scherzer, Optik 2, 1947, pp. 114-132.

*Primary Examiner* — Loha Ben
(74) *Attorney, Agent, or Firm* — The Webb Law Firm

(57) ABSTRACT

A spherical aberration corrector is offered which permits a correction of deviation of the circularity of at least one of an image and a diffraction pattern and a correction of on-axis aberrations to be carried out independently. The spherical aberration corrector (100) is for use with a charged particle beam instrument (1) for obtaining the image and the diffraction pattern and has a hexapole field generating portion (110) for producing plural stages of hexapole fields, an octopole field superimposing portion (120) for superimposing an octopole on at least one of the plural stages of hexapole fields to correct deviation of the circularity of at least one of the image and diffraction pattern, and a deflection portion (130) for deflecting a charged particle beam.

13 Claims, 20 Drawing Sheets

(51) Int. Cl.
  *H01J 3/26* (2006.01)
  *G02B 27/00* (2006.01)
  *H01J 3/12* (2006.01)
  *H01J 37/05* (2006.01)
  *H01J 37/147* (2006.01)
  *H01J 37/153* (2006.01)
  *H01J 37/28* (2006.01)
  *G21K 1/08* (2006.01)
  *G01N 23/20* (2006.01)
  *G02B 27/42* (2006.01)
  *H01J 3/04* (2006.01)

(56) References Cited

U.S. PATENT DOCUMENTS

| | | | | |
|---|---|---|---|---|
| 6,191,423 B1* | 2/2001 | Krijn | ................ | H01J 3/153 250/396 ML |
| 6,852,983 B2* | 2/2005 | Matsuya | ................ | H01J 37/153 250/396 ML |
| 7,015,481 B2* | 3/2006 | Matsuya | ................ | H01J 37/28 250/310 |
| 7,211,804 B2* | 5/2007 | Yoshida | ................ | H01J 37/153 250/310 |
| 7,619,218 B2* | 11/2009 | Nakano | ................ | H01J 37/153 250/306 |
| 7,763,862 B2* | 7/2010 | Hosokawa | .......... | H01J 37/1472 250/396 ML |
| 8,035,086 B2* | 10/2011 | Hirayama | ................ | H01J 3/12 250/396 ML |
| 8,067,732 B2* | 11/2011 | Nakasuji | ................ | H01J 37/05 250/306 |
| 8,314,402 B2* | 11/2012 | Zach | .................... | H01J 37/153 250/396 ML |
| 8,729,491 B2* | 5/2014 | Dohi | ........................ | H01J 3/26 250/306 |

* cited by examiner

SPHERICAL ABERRATION CORRECTOR, METHOD OF SPHERICAL ABERRATION CORRECTION, AND CHARGED PARTICLE BEAM INSTRUMENT

BACKGROUND OF THE INVENTION

1. Field of the Invention

The present invention relates to a spherical aberration corrector, method of spherical aberration correction, and charged particle beam instrument.

2. Description of Related Art

Spherical aberration correctors of the two stage three-fold-field type, i.e., using thick fields having three-fold symmetry (that is, using three-fold symmetric fields having a thickness along the optical axis), are used as spherical aberration correctors in electron microscopes such as transmission electron microscopes (TEM) and scanning transmission electron microscopes (STEM).

It is known that, if two-fold astigmatism is induced at an optically different plane, a deviation of the circularity of an image (deviation in aspect ratio) or a deviation of the circularity of a diffraction pattern occurs (see, for example, O. Scherzer, Optik 2 (1947), 114).

The spherical aberration corrector of the two stage three-fold-field type uses an optical system employing a thick field of three-fold symmetry and, therefore, if an axial misalignment occurs within a multipolar field, a field of two-fold symmetry is generated in a plane different from a reciprocal space that forms the center of the multipolar field due to an axial misalignment of three-fold astigmatism. This may cause a deviation of the circularity of the image or diffraction pattern.

A spherical aberration corrector of the two stage three-fold-field type is generally fitted with a deflection system for deflecting the electron beam in two dimensions for alignment. It is possible to correct the deviation of the circularity of the image or diffraction pattern using the deflection system.

On the other hand, a spherical aberration corrector needs to correct on-axis aberrations including two-fold astigmatism, on-axis comatic aberration, star aberration, and four-fold astigmatism.

For example, JP-A-2013-30278 discloses a spherical aberration corrector having two multipolar coils for producing a hexapole field and two axisymmetric lenses (transfer lenses) interposed between the coils. This known spherical aberration corrector corrects spherical aberration Cs in an objective lens but it is stated that parasitic aberrations (such as first-order astigmatism of two-fold symmetry, second-order comatic aberration of one-fold symmetry, second-order astigmatism of three-fold symmetry, third-order star aberration of two-fold symmetry, and third-order astigmatism of four-fold symmetry) are produced due to positional deviations of polar elements constituting multipolar lenses and magnetic characteristic variations of the material of the polar elements.

In the spherical aberration corrector, on-axis aberrations are generally corrected by the above-described deflection system.

In this way, the spherical aberration corrector can carry out a correction of deviation of the circularity of an image or diffraction pattern and a correction of on-axis aberrations by means of the above-described deflection system. However, in the spherical aberration corrector, a correction of deviation of the circularity of an image or diffraction pattern and a correction of on-axis aberrations must be made using the same deflection system.

Accordingly, the deflection system must be so adjusted that both of deviation of the circularity of an image or diffraction pattern and on-axis aberrations are corrected. This may complicate the adjustment. Furthermore, such an adjustment for correcting both of the deviation of the circularity and the on-axis aberrations may not be possible to achieve. Consequently, the effects of deviation of the circularity of an image or diffraction pattern and the effects of on-axis aberrations may be not reduced.

Therefore, there is a demand for a spherical aberration corrector permitting a correction of deviation of the circularity of an image or diffraction pattern and a correction of on-axis aberrations to be carried out independently.

SUMMARY OF THE INVENTION

One object associated with some aspects of the present invention is to provide a spherical aberration corrector and spherical aberration correction method permitting a correction of a deviation of the circularity of at least one of an image and a diffraction pattern and a correction of on-axis aberrations to be carried out independently.

Another object associated with some aspects of the invention is to provide a charged particle beam instrument including the spherical aberration corrector described in the immediately preceding paragraph.

(1) A spherical aberration corrector associated with the present invention is for use with or in a charged particle beam instrument for obtaining an image and a diffraction pattern. The spherical aberration corrector has: a hexapole field generating portion for producing plural stages of hexapole fields; an octopole field superimposing portion for superimposing an octopole field on at least one of the plural stages of hexapole fields to correct deviation of the circularity of at least one of the image and diffraction pattern; and a deflection portion for deflecting a charged particle beam.

This spherical aberration corrector permits a correction of on-axis aberrations and a correction of deviation of the circularity of at least one of the image and diffraction pattern to be carried out independently.

(2) In one feature of this spherical aberration corrector, the deflection portion may adjust the tilt of the charged particle beam within the hexapole field such that four-fold astigmatism induced by the octopole field is corrected.

In this spherical aberration corrector, the four-fold astigmatism induced by the octopole field produced by the octopole field superimposing portion is corrected by tilting the charged particle beam by means of the deflection portion. As a result, deviation of the circularity of at least one of the image and diffraction pattern can be corrected. Hence, a correction of on-axis aberrations and a correction of deviation of the circularity of at least one of the image and diffraction pattern can be carried out independently.

(3) Another spherical aberration corrector associated with the present invention is for use with or in a charged particle beam instrument for obtaining an image and a diffraction pattern. The spherical aberration corrector has: a hexapole field generating portion for producing plural stages of hexapole fields; a quadrupole field superimposing portion for superimposing a quadrupole field on at least one of the plural stages of hexapole fields to correct deviation of the circularity of at least one of the image and diffraction pattern; and a deflection portion for deflecting a charged particle beam.

This spherical aberration corrector permits a correction of on-axis aberrations and a correction of deviation of the circularity of at least one of the image and diffraction pattern to be carried out independently.

(4) In one feature of this spherical aberration corrector, the deflection portion may adjust the tilt of the charged particle beam within the hexapole field such that star aberration induced by the quadrupole field is corrected.

In this spherical aberration corrector, star aberration induced by the quadrupole field produced by the quadrupole field superimposing portion is corrected by tilting the charged particle beam by means of the deflection portion. As a result, deviation of the circularity of at least one of the image and diffraction pattern can be corrected. Hence, a correction of on-axis aberrations and a correction of deviation of the circularity of at least one of the image and diffraction pattern can be carried out independently.

(5) A further spherical aberration corrector associated with the present invention is for use with or in a charged particle beam instrument for obtaining an image and a diffraction pattern. The spherical aberration corrector has: a hexapole field generating portion for producing plural stages of hexapole fields; a deflecting field superimposing portion for superimposing a deflecting field on at least one of the plural stages of hexapole fields to correct deviation of the circularity of at least one of the image and diffraction pattern; and a deflection portion for deflecting a charged particle beam.

This spherical aberration corrector permits a correction of on-axis aberrations and a correction of deviation of the circularity of at least one of the image and diffraction pattern to be carried out independently.

(6) In one feature of this spherical aberration corrector, the deflection portion may adjust the tilt of the charged particle beam within the hexapole field such that star aberration induced by the deflecting field is corrected.

In this spherical aberration corrector, star aberration induced by the deflecting field produced by the deflecting field superimposing portion is corrected by tilting the charged particle beam by means of the deflection portion. As a result, deviation of the circularity of at least one of the image and diffraction pattern can be corrected. Hence, a correction of on-axis aberrations and a correction of deviation of the circularity of at least one of the image and diffraction pattern can be carried out independently.

(7) In one feature of any one of these spherical aberration correctors, the hexapole field generating portion may have two stages of multipole elements.

(8) In one feature of this spherical aberration corrector, there may be further provided transfer lenses disposed between the two stages of multipole elements.

(9) A method of spherical aberration correction associated with the present invention is implemented by a charged particle beam instrument for obtaining an image and a diffraction pattern. The method starts with producing plural stages of hexapole fields. An octopole field is superimposed on at least one of the hexapole fields to correct deviation of the circularity of at least one of the image and the diffraction pattern. A charged particle beam is deflected to adjust the tilt of the beam within the hexapole field such that four-fold astigmatism induced by the octopole field is corrected.

In this method of spherical aberration correction, four-fold astigmatism induced by the superimposed octopole field is corrected by tilting the charged particle beam. As a result, deviation of the circularity of at least one of the image and diffraction pattern can be corrected. Hence, a correction of on-axis aberrations and a correction of deviation of the circularity of at least one of the image and diffraction pattern can be carried out independently.

(10) Another method of spherical aberration correction associated with the present invention is implemented by a charged particle beam instrument for obtaining an image and a diffraction pattern. The method starts with producing plural stages of hexapole fields. A quadrupole field is superimposed on at least one of the hexapole fields to correct deviation of the circularity of at least one of the image and the diffraction pattern. A charged particle beam is deflected to adjust the tilt of the beam within the hexapole field such that star aberration induced by the quadrupole field is corrected.

In this method of spherical aberration correction, star aberration induced b$_y$, the superimposed quadrupole field is corrected by tilting the charged particle beam. As a result, deviation of the circularity of at least one of the image and diffraction pattern can be corrected. Hence, a correction of on-axis aberrations and a correction of deviation of the circularity of at least one of the image and diffraction pattern can be carried out independently.

(11) A further method of spherical aberration correction associated with the present invention is implemented by a charged particle beam instrument for obtaining an image and a diffraction pattern. The method starts with producing plural stages of hexapole fields. A deflecting field is superimposed on at least one of the hexapole fields to correct deviation of the circularity of at least one of the image and the diffraction pattern. A charged particle beam is deflected to adjust the tilt of the beam within the hexapole field such that star aberration induced by the deflecting field is corrected.

In this method of spherical aberration correction, star aberration induced by the superimposed deflecting field is corrected by tilting the charged particle beam. As a result, deviation of the circularity of at least one of the image and diffraction pattern can be corrected. Hence, a correction of on-axis aberrations and a correction of deviation of the circularity of at least one of the image and diffraction pattern can be carried out independently.

(12) In one feature of this method of spherical aberration correction, the plural stages of hexapole fields may be two stages of hexapole fields.

(13) A charged particle beam instrument associated with the present invention includes a spherical aberration corrector associated with the present invention.

This charged particle beam instrument includes the spherical aberration corrector associated with the present invention and, therefore, it is possible to obtain good image and diffraction pattern less affected by the effects of spherical aberration, on-axis aberrations, and deviation of the circularity of at least one of the image and diffraction pattern.

DESCRIPTION OF THE INVENTION

The preferred embodiments of the present invention are hereinafter described in detail with reference to the drawings. It is to be understood that the embodiments provided below do not unduly restrict the scope and content of the present invention delineated by the appended claims and that not all the configurations described below are essential constituent components of the invention.

1. First Embodiment 1.1. Spherical Aberration Corrector

Figure 1:
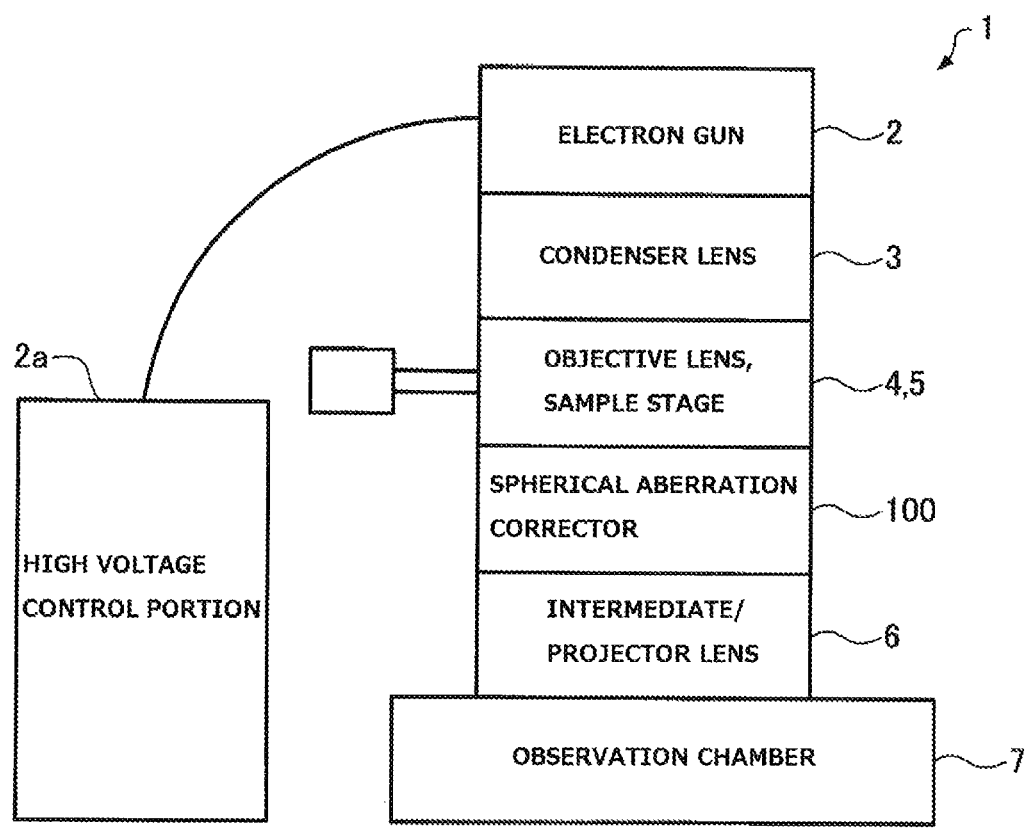
FIG. 1 is a block diagram of a charged particle beam instrument including a spherical aberration corrector associated with a first embodiment of the present invention.

A spherical aberration corrector associated with a first embodiment of the present invention is first described by referring to FIG. 1, which shows the configuration of a charged particle beam instrument 1 including the spherical aberration corrector, 100.

The spherical aberration corrector 100 is for use with a charged particle beam instrument that is a microscope for obtaining magnified images and diffraction patterns by directing charged particles such as electrons or ions at a subject under observation. For example, the charged particle beam instrument is a transmission electron microscope (TEM), a scanning transmission electron microscope (STEM), a scanning electron microscope (SEM), or the like. In this example, the charged particle beam instrument 1 is a transmission electron microscope (TEM).

As shown in FIG. 1, the charged particle beam instrument 1 includes the spherical aberration corrector 100 that operates as a spherical aberration corrector for the imaging system of the charged particle beam instrument 1 in the example of FIG. 1. Furthermore, the spherical aberration corrector 100 permits at least one of a correction of on-axis aberrations (two-fold astigmatism, on-axis comatic aberration, star aberration, and four-fold astigmatism) and a correction of deviation of the circularity of at least one of an image and a diffraction pattern to be carried out. In the following example, the spherical aberration corrector 100 performs both a correction of on-axis aberrations and a correction of deviation of the circularity of a diffraction pattern.

Furthermore, the charged particle beam instrument 1 includes an electron gun 2, condenser lenses 3, an objective lens 4, a sample stage 5, an intermediate/projector lens 6, and an observation chamber 7.

The electron gun 2 generates and emits an electron beam by accelerating electrons released from a cathode by means of an anode. A high-voltage power supply is provided to the electron gun 2 from a high voltage control portion 2a. A thermionic electron gun, a thermal field emission electron gun, a cold field emission gun, or the like can be used as the electron gun 2.

The condenser lenses 3 are disposed behind (on the downstream side along the electron beam) the electron gun 2. The condenser lenses 3 focus the electron beam generated by the electron gun 2. The condenser lenses 3 constitute an illumination lens system for directing the electron beam at a sample on the sample stage 5. The electron beam focused by the condenser lenses 3 reaches the objective lens 4 and the sample stage 5.

The objective lens 4 is disposed behind the condenser lenses 3. The objective lens 4 is an initial stage of lens for bringing the electron beam transmitted through the sample into focus. Objective minilenses 4a and 4b (see FIG. 2) may be disposed between the objective lens 4 and the spherical aberration corrector 100.

The sample stage 5 can hold the sample thereon. The electron beam transmitted through the sample impinges on the spherical aberration corrector 100 via the objective lens 4.

The intermediate/projector lens 6 is disposed behind the spherical aberration corrector 100. The intermediate/projector lens 6 cooperates with the objective lens 4 to constitute an imaging lens system for imaging the electron beam transmitted through the sample. The intermediate/projector lens 6 focuses an image or diffraction pattern on a camera (not shown) mounted in the observation chamber 7.

The charged particle beam instrument 1 may be configured including a post collector lens 8 (see FIG. 2) disposed behind the spherical aberration corrector 100. The post collector lens 8 is used to focus an image of the sample onto a selected area aperture plane SA (see FIG. 2).

The spherical aberration corrector 100 is positioned between the objective lens 4 and the intermediate/projector lens 6. The spherical aberration corrector 100 can correct spherical aberration in the imaging system (i.e., the objective lens 4). Furthermore, the spherical aberration corrector 100 can correct on-axis aberrations and deviation of the circularity of the diffraction pattern which are produced concomitantly with correction of spherical aberration.

A circularity deviation referred to herein is a deviation from a true circle when an object to be observed as a true circle (perfect circle) is not observed as a true circle. Where there is a deviation in the circularity of a diffraction pattern, a Debye ring to be observed as a true circle is observed as a distorted circle, for example.

Figure 2:
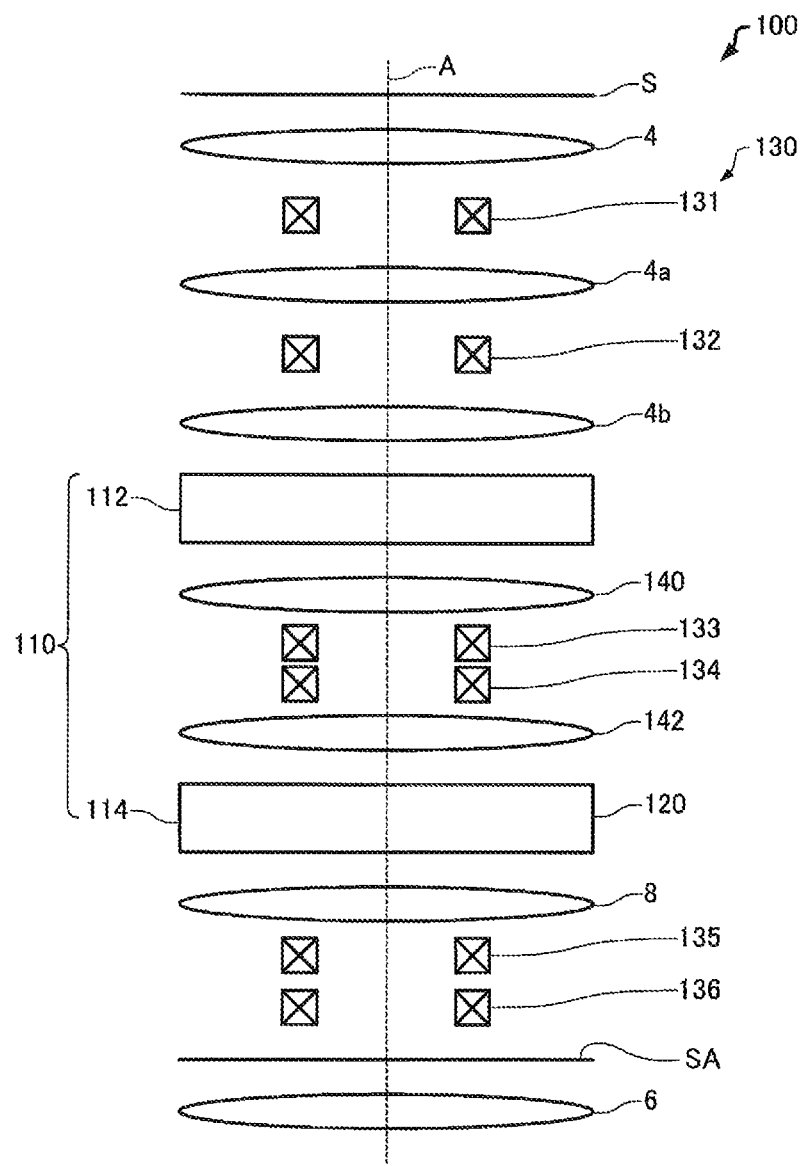
FIG. 2 is a schematic diagram of an optical system for use in the spherical aberration corrector shown in FIG. 1.

FIG. 2 is a diagram showing one example of optical system of the spherical aberration corrector 100. FIG. 2 shows the part of the optical system which exists between the sample plane S of the charged particle beam instrument 1 at which the sample is placed and the intermediate/projector lens 6.

As shown in FIG. 2, the spherical aberration corrector 100 is configured including a hexapole field generating portion 110, an octopole field superimposing portion 120, a deflection portion 130, and transfer lenses 140, 142.

The hexapole field generating portion 110 produces plural stages of hexapole fields (i.e., a three-fold symmetric field). In the illustrated example, the hexapole field generating portion 110 produces two stages of hexapole fields. The hexapole field generating portion 110 may produce three or more stages of hexapole fields.

The hexapole field generating portion 110 is configured including multipole elements arranged in plural stages. In the illustrated example, the hexapole field generating portion 110 is configured including two stages of multipole elements, i.e., a first multipole element 112 and a second multipole element 114. In the hexapole field generating portion 110, two stages of hexapole fields are generated using the first multipole element 112 and the second multipole element 114.

Each of the first multipole element 112 and second multipole element 114 is a dodecapole (12-pole) element, for example. No restriction is placed on the number of poles of each of the first multipole element 112 and second multipole element 114. A multipolar field produced by each of the first multipole element 112 and second multipole element 114 is any one of a static magnetic field, a static electric field, a field produced by superimposing static magnetic and electric fields. In the following description, a multipolar field produced by each of the first multipole element 112 and second multipole element 114 is a static magnetic field.

Figure 3:
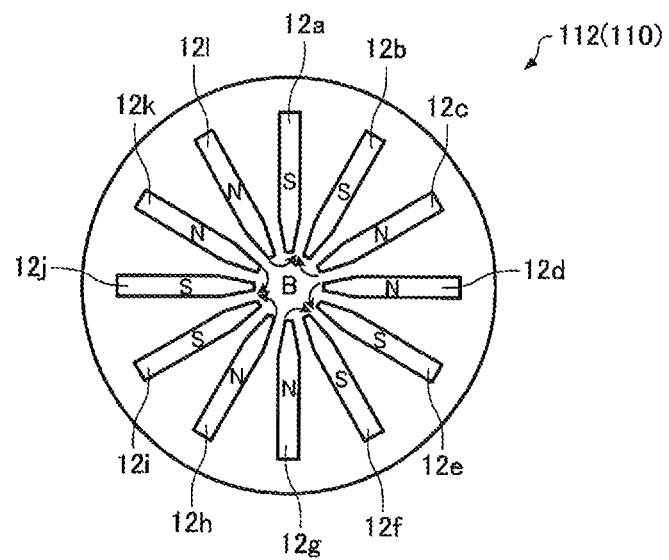
FIG. 3 shows one example of arrangement of magnetic poles in a first multipole element for producing a hexapole field.
Figure 4:
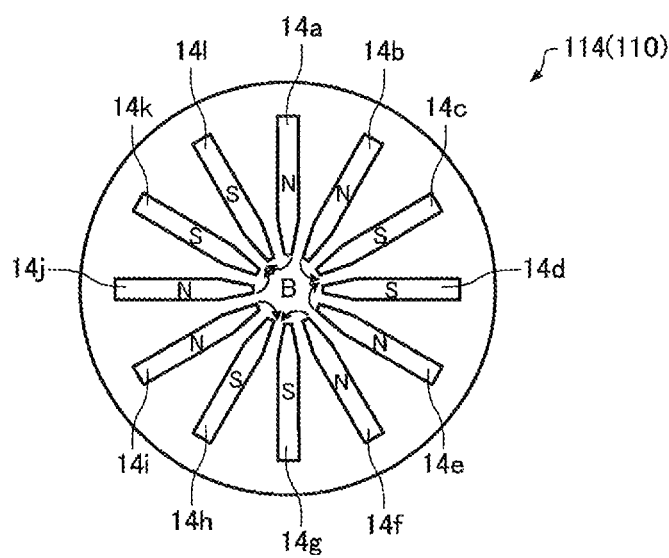
FIG. 4 shows one example of arrangement of magnetic poles in a second multipole element for producing a second hexapole field.

FIG. 3 is a diagram showing one example of arrangement of magnetic poles of the first multipole element 112 for producing a hexapole field. FIG. 4 is a diagram showing one example of arrangement of magnetic poles of the second multipole element 114 for producing a hexapole field.

As shown in FIG. 3, the first multipole element 112 has 12 magnetic poles 12a, 12b, 12c, 12d, 12e, 12f, 12g, 12h, 12i, 12j, 12k, and 12l radially arranged about an optical axis A (see FIG. 2). That is, the poles 12a-12l are angularly spaced from each other by 30 degrees about the optical axis A.

As shown in FIG. 4, the second multipole element 114 has 12 magnetic poles 14a, 14b, 14c, 14d, 14e, 14f, 14g, 14h, 14i, 14j, 14k, and 14l radially arranged about the optical axis A (see FIG. 2). That is, the magnetic poles 14a-14l are angularly spaced from each other by 30 degrees about the optical axis A.

The hexapole field generating portion 110 produces a hexapole field by supplying given exciting currents to excitation coils (not shown) mounted on the magnetic poles 12a-12l of the first multipole element 112. Similarly, the hexapole field generating portion 110 produces a second hexapole field by supplying given exciting currents to excitation coils (not shown) mounted on the magnetic poles 14a-14l of the second multipole element 114.

Each of the first multiple element 112 and second multipole element 114 produces a hexapole field by creating 6 magnetic poles placed symmetrically with respect to the optical axis A as shown in FIGS. 3 and 4. The first multiple element 112 and second multipole element 114 are opposite in polarity. In other words, the second multipole element 114 produces a hexapole field angularly shifted by 60 degrees about the optical axis A relative to the hexapole field produced by the first multipole element 112.

Each of the first multiple element 112 and second multipole element 114 has a thickness along the optical axis A. Therefore, multipolar fields produced by the first multipole element 112 and second multipole element 114 have thicknesses along the optical axis A. A multipole element having a thickness along the optical axis A generates a field by means of higher-order terms other than the primary term of the produced multipolar field. The thickness of the first multipole element 112 along the optical axis A and the thickness of the second multipole element 114 along the optical axis A may be identical or different.

The octopole field superimposing portion 120 superimposes an octopole field (i.e., a four-fold symmetric field) on the hexapole field generated by the hexapole field generating portion 110 to correct deviation of the circularity of the diffraction pattern. In the example of FIG. 2, the octopole field superimposing portion 120 superimposes an octopole field on the hexapole field generated by the second multipole element 114. The octopole field superimposing portion 120 produces the octopole field according to the magnitude of the deviation of the diffraction pattern. Four-fold astigmatism is induced as a result of the generation of the octopole field by the octopole field superimposing portion 120.

In the illustrated example, the octopole field superimposing portion 120 is configured including the second multipole element 114. The octopole field superimposing portion 120 produces an octopole field using the second multipole element 114.

Figure 5:
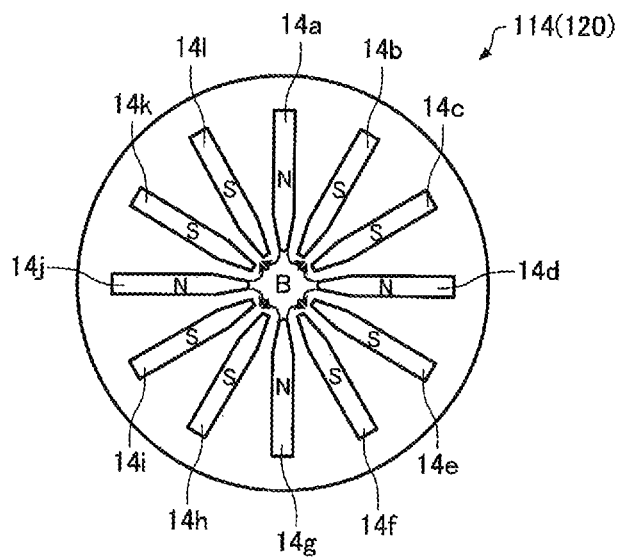
FIG. 5 shows one example of arrangement of magnetic poles in a second multipole element for producing an octopole field.

FIG. 5 shows an example of arrangement of the magnetic poles of the second multipole element 114 for producing an octopole field.

As shown in FIG. 5, the octopole field superimposing portion 120 produces an octopole field by supplying given excitation currents to excitation coils (not shown) mounted on the magnetic poles 14a-14l of the second multipole element 114. The second multipole element 114 produces an octopole field (a four-fold symmetric field) by creating 8 magnetic poles arranged symmetrically with respect to the optical axis A as shown in FIG. 5.

The second multipole element 114 produces hexapole and octopole fields as described previously. For this purpose, excitation coils for producing the hexapole field and excitation coils for producing the octopole field are mounted on the magnetic poles 14a-14l, respectively, of the second multipole element 114. By supplying respective given excitation currents to the excitation coils, the second multipole element 114 produces the hexapole and octopole fields. Thus, superimposed hexapole and octopole fields can be produced. Since the second multipole element 114 is a dodecapole element, this single multipole element alone can produce the hexapole field (three-fold symmetric field) and octopole field (four-fold symmetric field).

The deflection portion 130 deflects the electron beam. In particular, the deflection portion 130 can tilt the electron beam relative to the optical axis A within the hexapole fields produced by the multipole elements 112 and 114 by deflecting the beam. Consequently, on-axis aberrations, for example, can be corrected. Furthermore, the circularities of images and diffraction patterns can be varied by varying the magnitude of the tilt of the electron beam relative to the optical axis A within the multipole fields generated by the multipole elements 112 and 114, for the reason described later.

As shown in FIG. 2, the deflection portion 130 is configured including a set of deflection coils 131, 132 disposed between the objective lens 4 and the first multipole element 112, a set of deflection coils 133, 134 disposed between the first multipole element 112 and the second multipole element 114, and a set of deflection coils 135, 136 disposed between the second multipole element 114 and the intermediate/projector lens 6.

The electron beam incident on the multipolar field (i.e., hexapole field) produced by the first multipole element 112 is deflected in two dimensions by the deflection coils 131 and 132. The electron beam can be tilted relative to the optical axis A within the multipole field produced by the first multipole element 112 by the use of the deflection coils 131 and 132.

The electron beam incident on the multipolar field (i.e., superimposed hexapole and octopole fields) produced by the second multipole element 114 is deflected in two dimensions by the deflection coils 133 and 134. The electron beam can be tilted relative to the optical axis A within the multipolar field produced by the second multipole element 114 by the use of the deflection coils 133 and 134.

The electron beam exiting from the second multipole element 114 is deflected in two dimensions by the deflection coils 135 and 136. The beam exiting from the second multipole element 114 can be aligned to the optical axis A by the deflection coils 135 and 136.

The transfer lenses 140 and 142 are disposed between the first multipole element 112 and the second multipole element 114. Each of the transfer lenses 140 and 142 is a lens of transfer magnification, for example, of 1:1. A reciprocal space image formed by the first multipole element 112 is transferred to the second multipole element 114 by the transfer lenses 140 and 142.

The operation of the spherical aberration corrector 100 is next described.

The spherical aberration corrector 100 corrects spherical aberration using the two stages of hexapole fields produced by the hexapole field generating portion 110.

In particular, the hexapole field generating portion 110 produces the two stages of hexapole fields using the first multipole element 112 and the second multipole element 114. The first multipole element 112 produces the first stage of hexapole field, giving rise to negative spherical aberration and three-fold astigmatism. The second multipole element 114 produces the second stage of hexapole field so as to cancel out the three-fold astigmatism induced by the first multipole element 112. Consequently, the negative spherical aberration can be extracted. Spherical aberration in the imaging system (i.e., the objective lens 4) can be corrected by canceling out the positive spherical aberration in the imaging system (objective lens 4) by the negative spherical aberration.

Although spherical aberration is corrected by the two stages of hexapole fields in this way, on-axis aberrations (such as two-fold astigmatism, on-axis comatic aberration, star aberration, and four-fold astigmatism) may be produced due to positional deviations of the magnetic poles 12a-12l constituting the first multipole element 112, positional deviations of the magnetic poles 14a-14l constituting the second multipole element 114, and variations in magnetic characteristics of the material of the magnetic poles.

Each hexapole field used to correct spherical aberration has a thickness along the optical axis A. Therefore, if the electron beam is misaligned relative to the optical axis A, i.e., if an axial misalignment occurs, the circularities of image and diffraction pattern vary. This causes deviations in circularity of image and diffraction pattern. The reason why the circularities of image and diffraction pattern vary is described below using a model consisting of a multipole element M and having the same configuration as the multipole elements 112 and 114.

Figure 6:
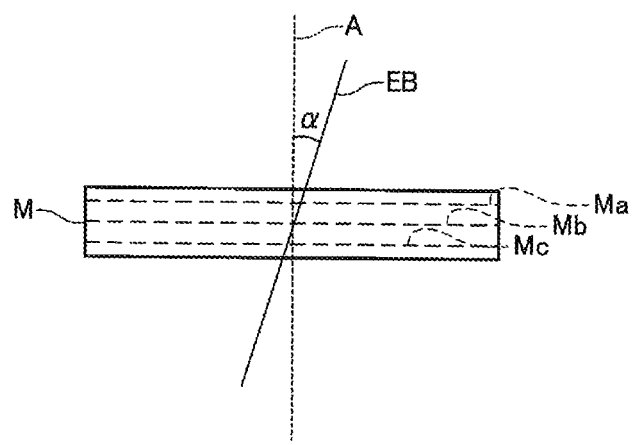
FIG. 6 is a schematic representation of a multipole element, illustrating the manner in which a hexapole field produced by the multipole element suffers from an axial misalignment.
Figure 7A:
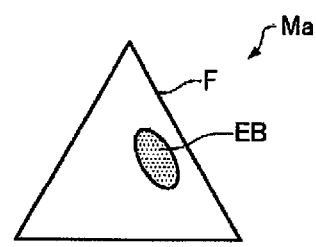
FIG. 7A is a schematic representation of the state of an electron beam on the top surface of a multipole element.
Figure 7B:
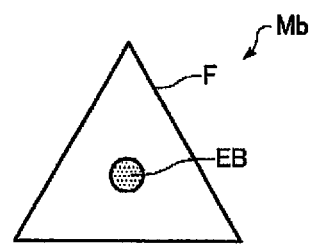
FIG. 7B is a schematic representation of the state of an electron beam in the central plane of the multipole element.
Figure 7C:
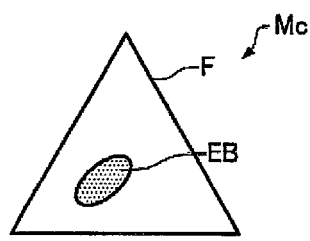
FIG. 7C is a schematic representation of the state of an electron beam on the bottom surface of the multipole element.

FIG. 6 schematically depicts the manner in which there is an axial misalignment in a hexapole field produced by the multipole element M. FIG. 7A is a schematic representation of the state of an electron beam EB on the top surface Ma of the multipole element M. FIG. 7B is a schematic representation of the state of the electron beam EB in the central plane Mb (diffraction plane equivalent to the reciprocal space) of the multipole element M. FIG. 7C is a schematic representation of the state of the electron beam EB on the bottom surface Mc of the multipole element M.

As shown in FIG. 6, if the electron beam EB is tilted relative to the optical axis A within a hexapole field F (see FIGS. 7A-7C) produced by the multipole element M and an axial misalignment occurs, quadrupole fields (two-fold symmetric fields) different in magnitude are produced on planes Ma and Mc, respectively, which are different from the central plane Mb of the multipole element M. As a result, different two-fold astigmatisms are induced at the top surface Ma and bottom surface Mc, respectively, as shown in FIGS. 7A-7C. This varies the circularities of the image and diffraction pattern, for the following reason. The multipole element M has an optically sufficient thickness and so observation of the central plane Mb of the multipole element M is optically different from observation of the ends (top surface Ma and bottom surface Mc) of the multipole element M. In this way, if different two-fold astigmatisms are induced at the two planes different from the central plane of the multipole element, the image and diffraction pattern vary in circularity.

In FIG. 6, the electron beam EB is tilted at an angle of a to the optical axis A in the hexapole field produced by the multipole element M. The circularities of the image and diffraction pattern vary according to the magnitude of the tilt angle α.

In this way, if spherical aberration is corrected using two stages of hexapole fields, on-axis aberrations and deviations in circularity of images and diffraction patterns occur in this way. The spherical aberration corrector 100 carries out a correction of on-axis aberrations and a correction of deviations of the circularities of diffraction patterns using the octopole field superimposing portion 120 and the deflection portion 130.

In particular, the octopole field superimposing portion 120 superimposes an octopole field (four-fold symmetric field) on the hexapole field produced by the second multipole element 114 to correct deviation of the circularity of the diffraction pattern. Consequently, four-fold astigmatism is induced.

The deflection portion 130 deflects the electron beam such that the tilt of tilt angle α (see FIG. 6) of the electron beam within the hexapole fields produced by the multipole elements 112 and 114 is sufficient to correct the induced four-fold astigmatism. That is, the deflection portion 130 tilts the electron beam within the hexapole fields by tilting the beam, thus correcting the four-fold astigmatism induced by the octopole field superimposing field 120.

As a result, given different two-fold astigmatisms are induced at the two planes different from the central plane (diffraction plane equivalent to a reciprocal plane) of the multipole elements 112 and 114. This varies the circularity of the diffraction pattern, thus correcting deviation of the circularity of the diffraction pattern.

In this way, in the spherical aberration corrector 100, the four-fold astigmatism induced by generation of an octopole field by the octopole field superimposing portion 120 is corrected by deflecting the electron beam by the deflection portion 130. As a result, deviation of the circularity of the diffraction pattern is varied. Consequently, deviation of the circularity of the diffraction pattern can be corrected independently of on-axis aberrations.

The spherical aberration corrector 100 and the charged particle beam instrument 1 have the following features.

The spherical aberration corrector 100 includes the hexapole field generating portion 110 for producing two stages of hexapole fields, the octopole field superimposing portion 120 for superimposing an octopole field on the hexapole field produced by the second multipole element 114 to correct deviation of the circularity of a diffraction pattern, and the deflection portion 130 for deflecting an electron beam. Consequently, deviation of the circularity of the diffraction pattern can be corrected independently of on-axis aberrations as described previously. Hence, a correction of on-axis aberrations and a correction of the circularity of a diffraction pattern can be carried out independently.

In the spherical aberration corrector 100, the deflection portion 130 adjusts the tilt of the electron beam within the hexapole fields produced by the multipole elements 112 and 114 such that the four-fold astigmatism induced by the octopole field produced by the octopole field superimposing portion 120 is corrected. As a result, the four-fold astigmatism induced by the octopole field produced by the octopole field superimposing portion 120 is corrected by deflecting the electron beam by means of the deflection portion 130. This makes it possible to correct deviation of the circularity of the diffraction pattern. In consequence, a correction of on-axis aberrations and a correction of deviation of the circularity of the diffraction pattern can be carried out independently.

Since the charged particle beam instrument 1 is configured including the spherical aberration corrector 100 permitting a correction of on-axis aberrations and a correction of deviation of the circularity of a diffraction pattern to be carried out independently, good images and diffraction patterns less affected by the effects of spherical aberration, on-axis aberrations, deviations of the circularities of the diffraction patterns can be obtained.

1.2. Method of Spherical Aberration Correction

Figure 8:
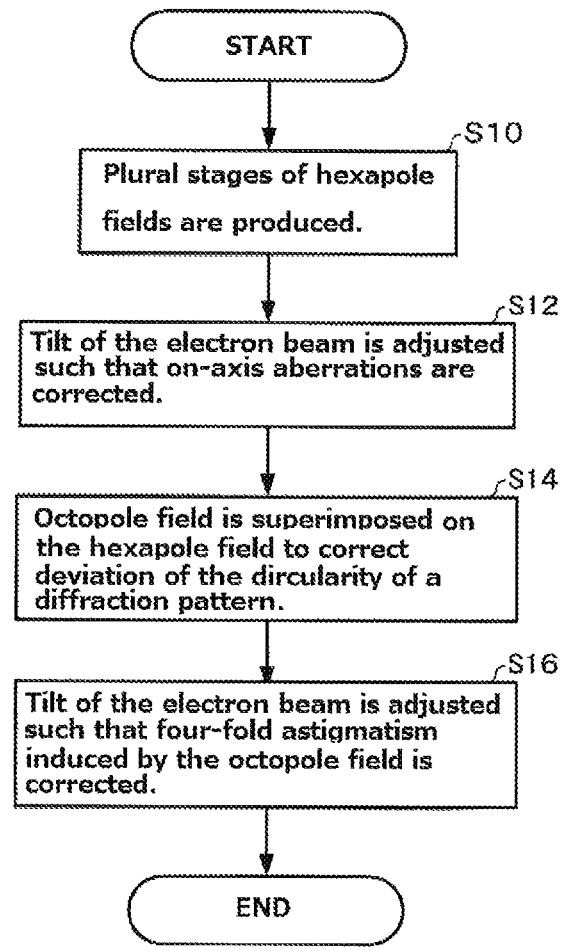
FIG. 8 is a flowchart illustrating one method of spherical aberration correction implemented in a spherical aberration corrector associated with the first embodiment.

A method of spherical aberration correction implemented by the spherical aberration corrector 100 associated with the first embodiment is next described by referring to the flowchart of FIG. 8 illustrating one example of this method.

First, the hexapole field generating portion 110 produces plural stages of hexapole fields (step S10). In particular, the hexapole field generating portion 110 produces two stages of hexapole fields by the two stages of multipole elements 112 and 114. This produces a negative spherical aberration, thus correcting spherical aberration in the imaging system (objective lens 4).

Then, the deflection portion 130 deflects the electron beam to adjust the tilt of the beam relative to the optical axis A within the hexapole fields produced by the multipole elements 112 and 114 such that on-axis aberrations are corrected (step S12). That is, on-axis aberrations are corrected by the deflection portion 130 by deflecting the electron beam.

Then, the octopole field superimposing portion 120 superimposes an octopole field on the hexapole field produced by the second multipole element 114 to correct deviation of the circularity of a diffraction pattern (step S14). The octopole field superimposing portion 120 produces the octopole field corresponding to the magnitude of the deviation of the circularity of the diffraction pattern. Since the octopole field superimposing portion 120 produces the octopole field, four-fold astigmatism is induced.

At step S14, the octopole field superimposing portion 120 superimposes an octopole field corresponding to the deviation of the circularity of the diffraction pattern. In particular, information about the deviation (direction and magnitude of the deviation) of the circularity of the diffraction pattern may be obtained from the obtained diffraction pattern. The intensity and direction of the octopole field produced by the octopole field superimposing portion 120 may be determined, based on the obtained information about the deviation of the circularity. At this time, the intensity and direction of the octopole field may be determined, based on data about correlations of deviations of the circularities of previously prepared diffraction patterns to intensities and directions of octopole fields.

Then, the deflection portion 130 deflects the electron beam to adjust the tilt of the electron beam relative to the optical axis A within the hexapole fields produced by the hexapole field generating portion 110 such that four-fold astigmatism induced by the octopole field produced by the octopole field superimposing portion 120 is corrected (S16). Consequently, the four-fold astigmatism induced by the octopole field produced by the octopole field superimposing portion 120 is cancel out, thus correcting the deviation of the circularity of the diffraction pattern.

No restriction is placed on the order in which the steps S12, S14, and S16 are performed.

Spherical aberration can be corrected by the processing steps described so far.

The method of spherical aberration correction implemented by the spherical aberration corrector 100 associated with the first embodiment involves the step S14 for superimposing an octopole field on one of two stages of hexapole fields to correct deviation of the circularity of a diffraction pattern and the step S16 for deflecting the electron beam to adjust the tilt of the beam within the hexapole field such that four-fold astigmatism induced by an octopole field is corrected. Consequently, a correction of on-axis aberrations and a correction of deviation of the circularity of a diffraction pattern can be carried out separately.

1.3. Experimental Example

In the present experimental example, deviation of the circularity of a diffraction pattern was corrected using the charged particle beam instrument 1 equipped with the spherical aberration corrector 100 associated with the first embodiment. Polycrystalline gold was used as a sample.

Figure 9:
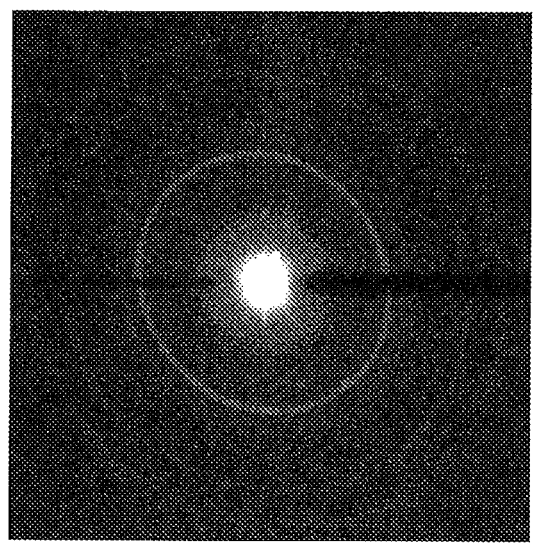
FIG. 9 is a diffraction pattern obtained from polycrystalline gold, and in which deviation of the circularity of the diffraction pattern is not yet corrected.
Figure 10:
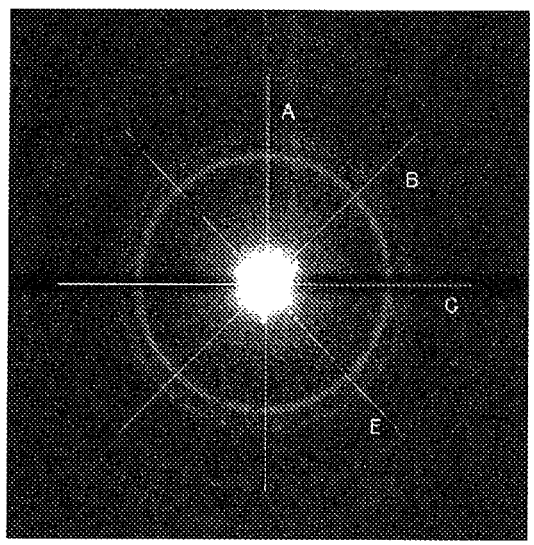
FIG. 10 is a diffraction pattern similar to FIG. 9, but in which the deviation of the circularity of the diffraction pattern has been corrected.

FIG. 9 shows a diffraction pattern (Debye ring) obtained from the polycrystalline gold before the deviation of the circularity of a diffraction pattern was corrected. FIG. 10 shows a diffraction pattern (Debye ring) obtained from the polycrystalline gold after correcting the deviation of the circularity of the diffraction pattern.

Before the deviation of the circularity of the pattern diffraction is corrected, a Debye ring corresponding to each crystalline plane is elliptical as shown in FIG. 9. After the deviation of the circularity of the diffraction pattern has been corrected, the Debye ring corresponding to individual crystalline planes is closer to a true circle than prior to the correction (see FIG. 9) as shown in FIG. 10. In the diffraction pattern shown in FIG. 10, corrections have been achieved such that the aspect ratio A/C and aspect ratio B/E are equal to or higher than 99%.

1.4. Modification

Figure 11:
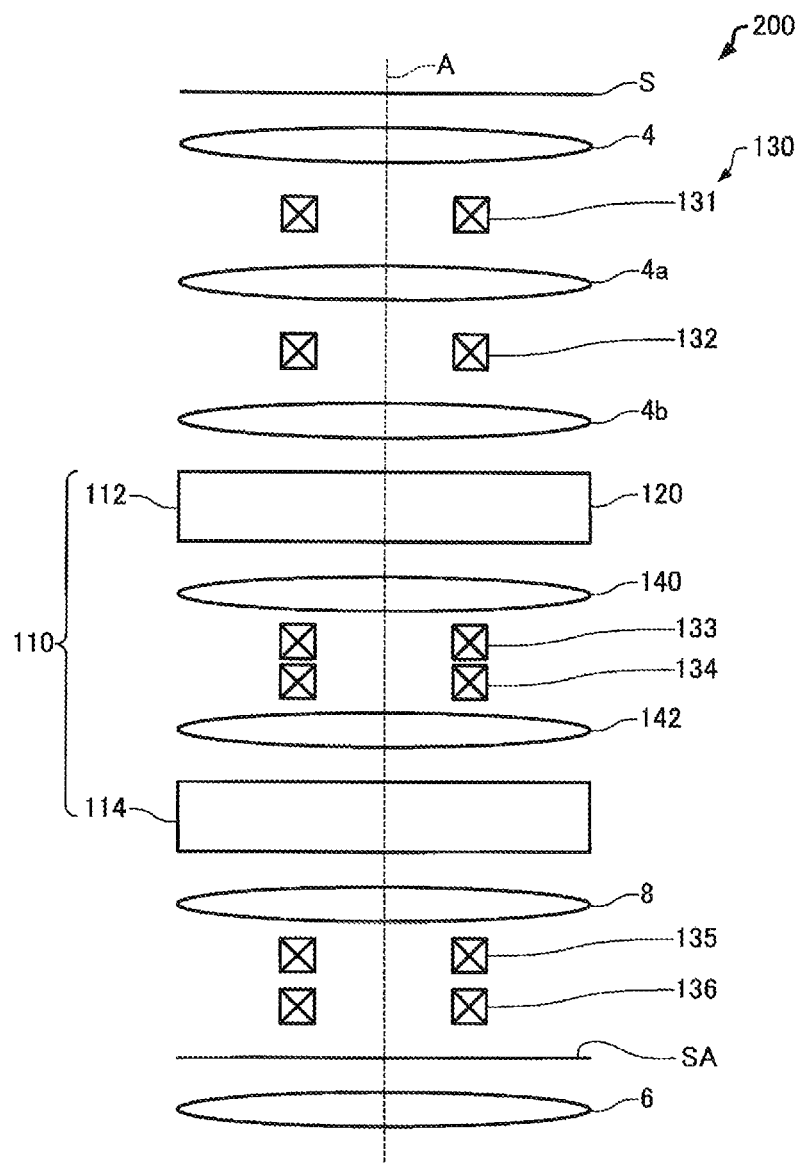
FIG. 11 is a schematic diagram of an optical system for use in a spherical aberration corrector associated with a modification of the first embodiment.

A modification of the first embodiment is next described by referring to FIG. 11, which shows the optical system of a spherical aberration corrector 200 associated with the modification of the first embodiment.

Those components of the spherical aberration corrector 200 associated with the modification of the first embodiment which are similar in function with their respective counterparts of the spherical aberration corrector 100 associated with the first embodiment are indicated by the same reference numerals as in the above-cited figures and a description thereof is omitted.

In the above-described spherical aberration corrector 100, the octopole field superimposing portion 120 is configured including the second multipole element 114 as shown in FIG. 2, the second multipole element 114 operating to produce superimposed hexapole and octopole fields.

In contrast, in the spherical aberration corrector 200, the octopole field superimposing portion 120 is configured including the first multipole element 112 as shown in FIG. 11. The first multipole element 112 produces superimposed hexapole and octopole fields.

The spherical aberration corrector 200 yields the same advantageous effects as the spherical aberration corrector 100.

2. Second Embodiment

2.1. Spherical Aberration Corrector

Figure 12:
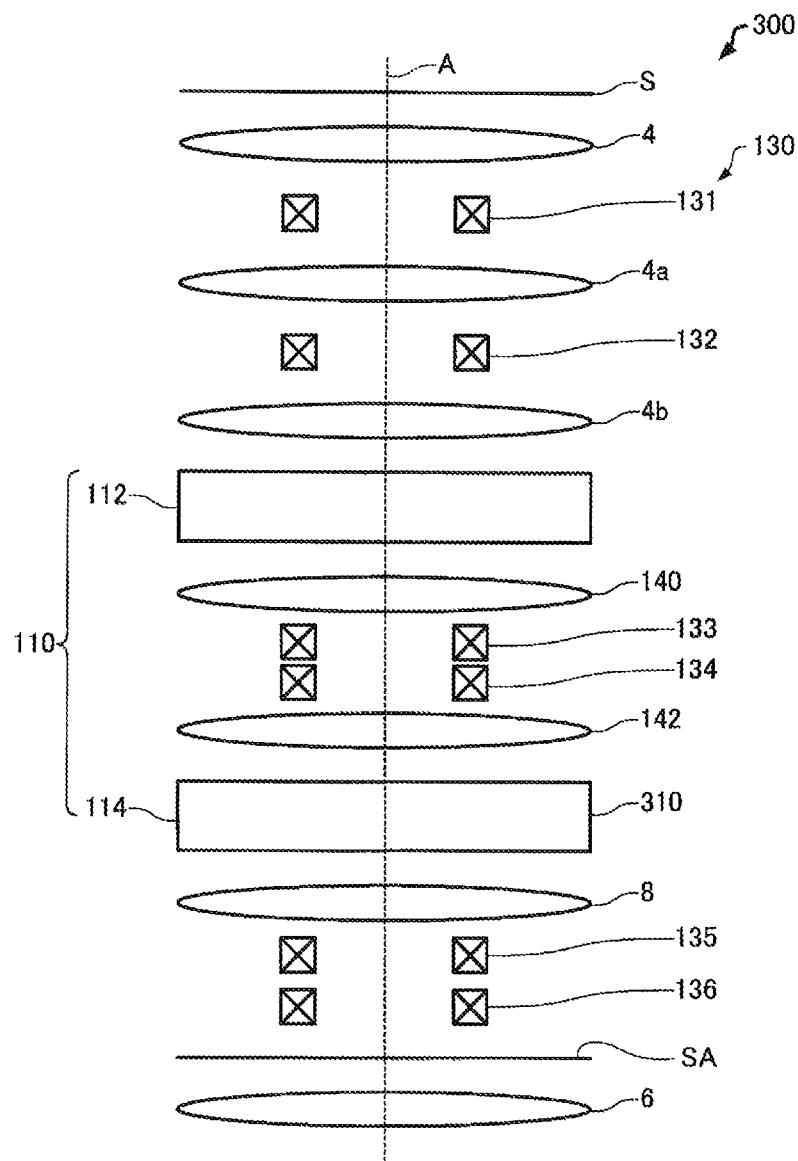
FIG. 12 is a schematic diagram of an optical system for use in a spherical aberration corrector associated with a second embodiment of the present invention.

A spherical aberration corrector associated with a second embodiment of the present invention is next described by referring to FIG. 12, which shows the optical system of the spherical aberration corrector, 300, associated with the second embodiment.

Those components of the spherical aberration corrector 300 associated with the second embodiment which are similar in function with their respective counterparts of the spherical aberration corrector 100 associated with the first embodiment are indicated by the same reference numerals as in the above-cited figures and a description thereof is omitted.

As shown in FIG. 2, the above-described spherical aberration corrector 100 has the octopole field superimposing portion 120. This octopole field superimposing portion 120 superimposes an octopole field on a hexapole field. The deflection portion 130 deflects the electron beam. Induced four-fold astigmatism is corrected. Deviation of the circularity of a diffraction pattern is corrected.

In contrast, the spherical aberration corrector 300 has a quadrupole field superimposing portion 310, which in turn superimposes a quadrupole field (i.e., two-fold symmetric field) on a hexapole field. The deflection portion 130 deflects the electron beam, corrects induced star aberration, and corrects deviation of the circularity of a diffraction pattern.

The quadrupole field superimposing portion 310 superimposes a quadrupole field on the hexapole field produced by the hexapole field superimposing portion 110 to correct deviation of the circularity of a diffraction pattern. In the illustrated example, the quadrupole field superimposing portion 310 superimposes a quadrupole field on a hexapole field produced by the second multipole element 114. The quadrupole field superimposing portion 310 produces a quadrupole field corresponding to the magnitude of the deviation of the circularity of the diffraction pattern. As a result, star aberration is induced.

The quadrupole field superimposing portion 310 produces the quadrupole field, for example, using a dodecapole element. In the illustrated example, the quadrupole field superimposing portion 310 is configured including the second multipole element 114. The quadrupole field superimposing portion 310 produces the quadrupole field by the use of the second multipole element 114.

Figure 13:
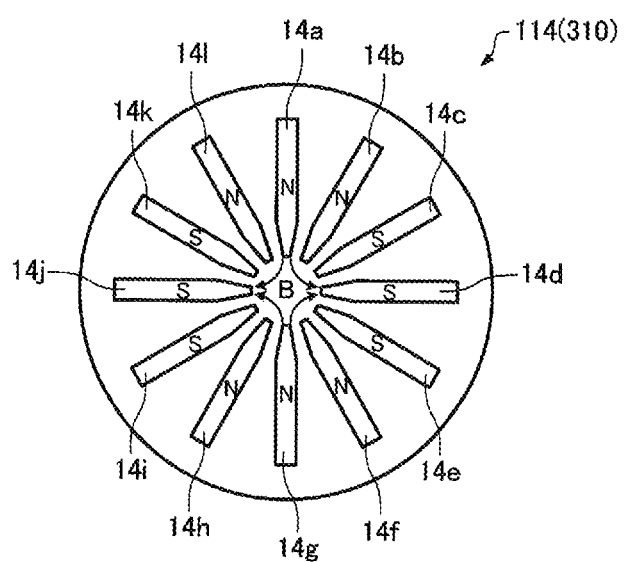
FIG. 13 shows one example of arrangement of magnetic poles in a second multipole element for producing a quadrupole field.

FIG. 13 shows one example of arrangement of magnetic poles of the second multipole element 114 for producing a quadrupole field.

As shown in FIG. 13, the quadrupole field superimposing portion 310 produces a quadrupole field by supplying given excitation currents to excitation coils (not shown) mounted on magnetic poles 14a-14l of the second multipole element 114. The second multipole element 114 produces a quadrupole field (two-fold symmetric field) by creating four magnetic poles arranged symmetrically with respect to the optical axis A.

As described previously, the second multipole element 114 produces hexapole and quadrupole fields. For this purpose, excitation coils for producing the hexapole field and excitation coils for producing the quadrupole field are mounted on the magnetic poles 14a-14l of the second multipole element 114. The second multipole element 114 produces the hexapole and quadrupole fields by supplying the given excitation currents to the excitation coils, respectively. Thus, superimposed hexapole and quadrupole fields can be created. Since the second multipole element 114 is a dodecapole element, this single multipole element alone can produce the hexapole field (three-fold symmetric field) and the quadrupole field (two-fold symmetric field).

The deflection portion 130 deflects the electron beam to adjust the tilt of the beam relative to the optical axis A within the hexapole fields produced by the multipole elements 112 and 114 such that star aberration induced by the quadrupole field produced by the quadrupole field superimposing portion 310 is corrected.

The operation of the spherical aberration corrector 300 is next described.

In the spherical aberration corrector 300, spherical aberration is corrected by the use of two stages of hexapole fields produced by the hexapole field generating portion 110 in the same way as for the above-described spherical aberration corrector 100.

Furthermore, in the spherical aberration corrector 300, a correction of on-axis aberrations and a correction of deviation of the circularity of a diffraction pattern are carried out by the quadrupole field superimposing portion 310 and the deflection portion 130.

In particular, the quadrupole field superimposing portion 310 superimposes a quadrupole field (two-fold symmetric field) on the hexapole field produced by the second multipole element 114 to correct deviation of the circularity of the diffraction pattern. As a result, star aberration is induced.

The deflection portion 130 deflects the electron beam to adjust the tilt of the beam within the hexapole fields produced by the multipole elements 112 and 114 such that the induced star aberration is corrected. That is, the deflection portion 130 tilts the beam within the hexapole fields by tilting the beam, thus correcting the star aberration induced by the quadrupole field superimposing portion 310.

As a result, given different two-fold astigmatisms are induced at two planes different from the central plane (diffraction plane equivalent to a reciprocal plane) of the multipole elements 112 and 114. The circularity of the diffraction pattern varies. Deviation of the circularity of the diffraction pattern is corrected.

In this way, in the spherical aberration corrector 300, the quadrupole field superimposing portion 310 produces a quadrupole field and thus star aberration is induced. The star aberration is corrected by deflecting the electron beam by means of the deflection portion 130. As a result, deviation of the circularity of the diffraction pattern is varied. Consequently, the deviation of the circularity of the diffraction pattern can be corrected independently of on-axis aberrations.

The spherical aberration corrector 300 has the following features.

The spherical aberration corrector 300 includes a hexapole field generating portion 110 for producing two stages of hexapole fields, a quadrupole field superimposing portion 310 for superimposing a quadrupole field on the hexapole field produced by the second multipole element 114 to correct deviation of the circularity of the diffraction pattern, and a deflection portion 130 for deflecting the electron beam. In consequence, deviation of the circularity of the diffraction pattern can be corrected independently of on-axis aberrations as described previously. Hence, a correction of on-axis aberrations and a correction of deviation of the circularity of the diffraction pattern can be carried out independently.

In the spherical aberration corrector 300, the deflection portion 130 adjusts the tilt of the electron beam within the hexapole fields produced by the multipole elements 112 and 114 such that star aberration induced by the quadrupole field superimposing portion 310 is corrected. The star aberration induced by the quadrupole field produced by the quadrupole field superimposing portion 310 is corrected by tilting the beam by means of the deflection portion 130. As a result, deviation of the circularity of the diffraction pattern can be corrected. Thus, a correction of on-axis aberrations and a correction of deviation of the circularity of the diffraction pattern can be carried out independently.

2.2. Method of Spherical Aberration Correction

Figure 14:
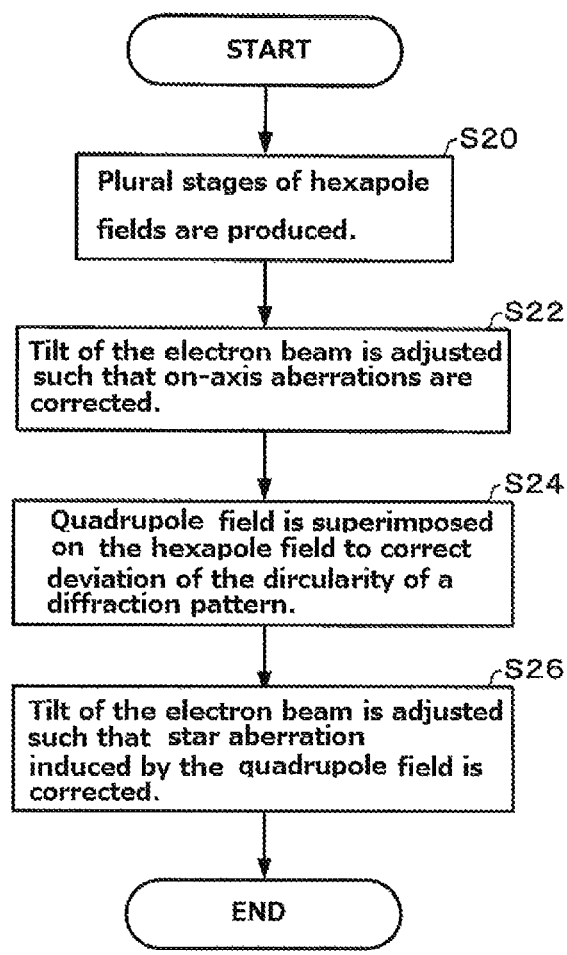
FIG. 14 is a flowchart illustrating one example of method of spherical aberration correction implemented in the spherical aberration corrector shown in FIG. 12.

A method of spherical aberration correction implemented by the spherical aberration corrector 300 associated with the second embodiment is next described by referring to FIG. 14, which is a flowchart illustrating one example of the method of spherical aberration correction implemented by the spherical aberration corrector 300.

First, the hexapole field generating portion 110 produces plural stages of hexapole fields (step S20). This results in a negative spherical aberration, correcting spherical aberration in the objective lens 4.

Then, the deflection portion 130 deflects the electron beam to adjust the tilt relative to the optical axis of the electron beam A within the hexapole fields produced by the multipole elements 112 and 114 such that on-axis aberrations are corrected (step S22). Consequently, the on-axis aberrations are corrected.

Then, the quadrupole field superimposing portion 310 superimposes a quadrupole field on the hexapole field produced by the second multipole element 114 to correct deviation of the circularity of the diffraction pattern (step S24). The quadrupole field superimposing portion 310 produces a quadrupole field corresponding to the magnitude of the deviation of the circularity of the diffraction pattern. The quadrupole field superimposing portion 310 produces the quadrupole field. This gives rise to star aberration.

Then, the deflection portion 130 deflects the electron beam to adjust the angle of the tilt of the electron beam within the hexapole field produced by the hexapole field generating portion 110 relative to the optical axis A such that the star aberration induced by the quadrupole field produced by the quadrupole field superimposing portion 310 is corrected (S26). Consequently, the star aberration induced by the quadrupole field produced by the quadrupole field superimposing portion 310 is canceled out. Deviation of the circularity of the diffraction pattern is corrected.

No restriction is imposed on the order in which the steps S22, S24, and S26 are performed.

Because of the processing steps, spherical aberration can be corrected.

The method of spherical aberration correction implemented by the spherical aberration corrector 300 associated with the second embodiment involves the step S24 for superimposing a quadrupole field on one of two stages of hexapole fields to correct deviation of the circularity of the diffraction pattern and the step S26 for deflecting the beam to adjust the tilt of the beam within the hexapole field such that star aberration induced by the quadrupole field is corrected. In consequence, a correction of on-axis aberrations and a correction of deviation of the circularity of the diffraction pattern can be carried out separately.

2.3. Modification

Figure 15:
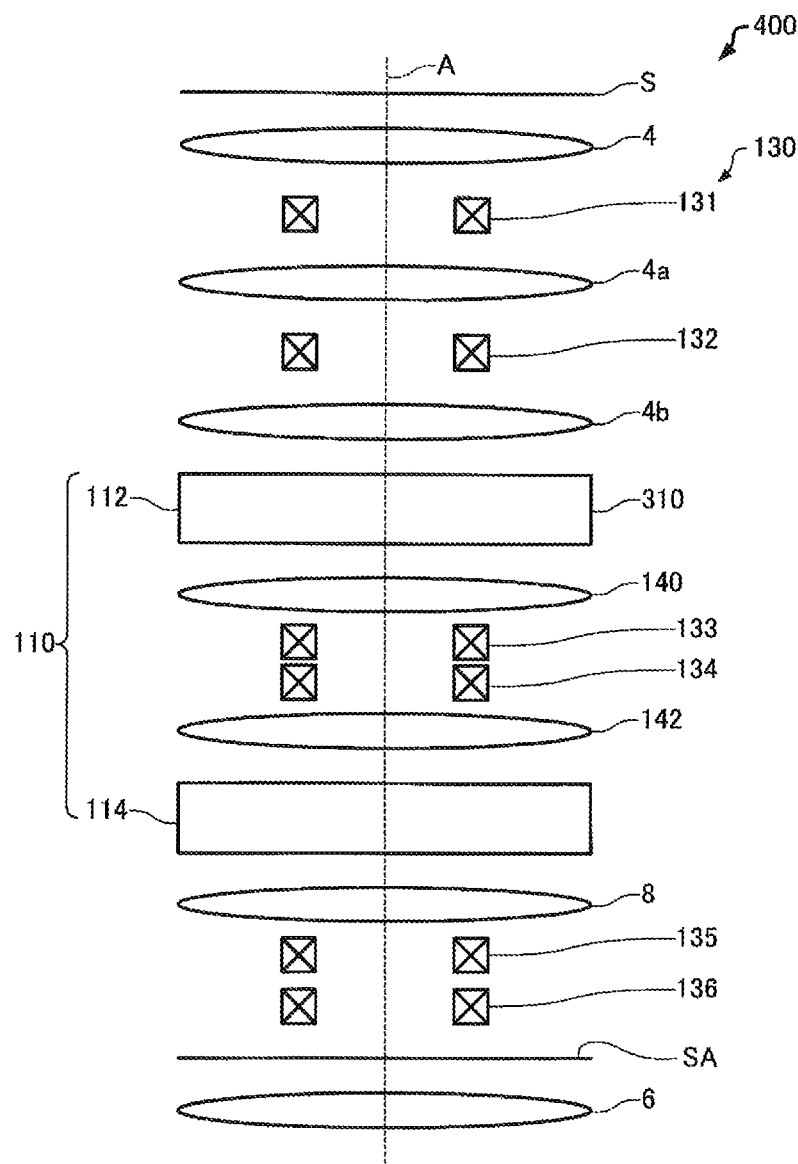
FIG. 15 is a schematic diagram of an optical system for use in a spherical aberration corrector associated with a modification of the second embodiment.

A modification of the second embodiment is next described by referring to FIG. 15, which shows the optical system of a spherical aberration corrector, 400, associated with the modification of the second embodiment.

Those components of the spherical aberration corrector 400 associated with the modification of the second embodiment which are similar in function with their respective counterparts of the spherical aberration corrector 300 associated with the second embodiment are indicated by the same reference numerals as in the above-cited figures and a description thereof is omitted.

As shown in FIG. 12, in the above-described spherical aberration corrector 300, the quadrupole field superimposing portion 310 is configured including the second multipole element 114. The second multipole element 114 creates superimposed hexapole and quadrupole fields.

In contrast, in the spherical aberration corrector 400, the quadrupole field superimposing portion 310 is configured including the first multipole element 112 as shown in FIG. 15. The first multipole element 112 produces superimposed hexapole and quadrupole fields.

The spherical aberration corrector 400 can yield the same advantageous effects as the spherical aberration corrector 300.

3. Third Embodiment

3.1. Spherical Aberration Corrector

Figure 16:
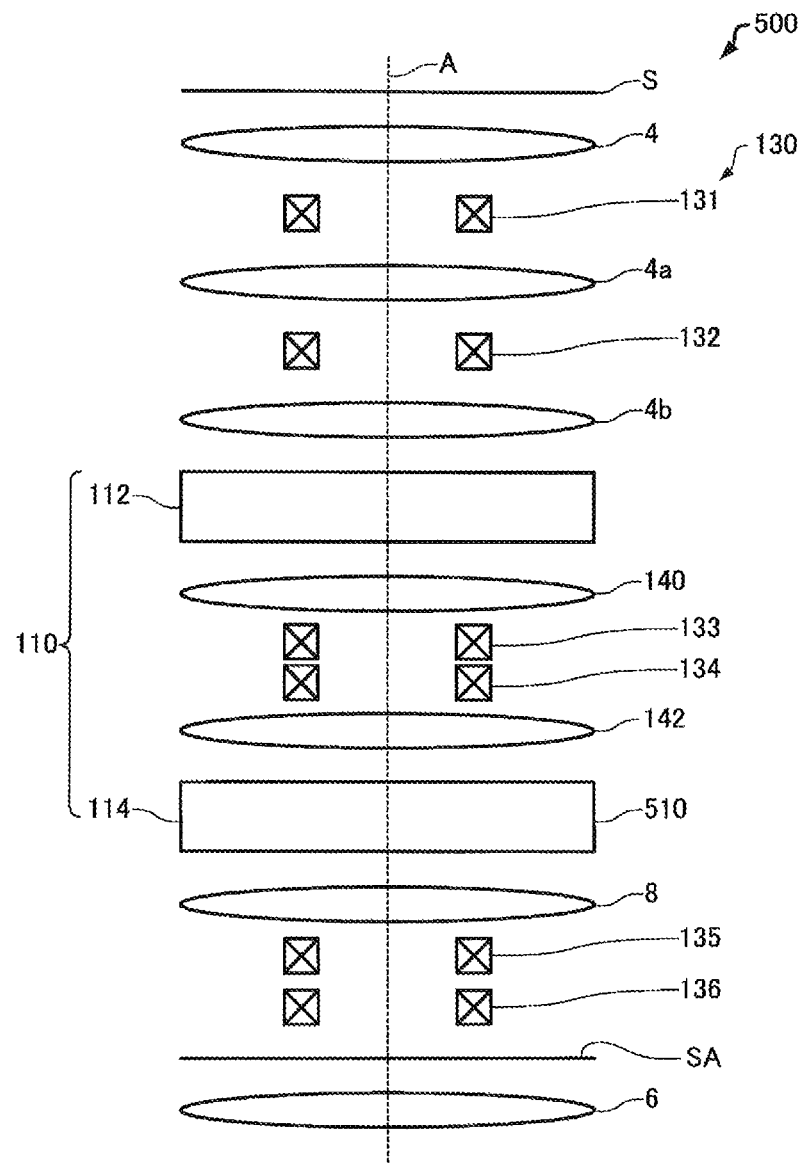
FIG. 16 is a schematic diagram of an optical system for use in a spherical aberration corrector associated with a third embodiment of the invention.

A spherical aberration corrector associated with a third embodiment of the present invention is next described by referring to FIG. 16, which shows the optical system of the spherical aberration corrector, 500.

Those components of the spherical aberration corrector 500 associated with the third embodiment which are similar in function with their respective counterparts of the spherical aberration corrector 100 associated with the first embodiment are indicated by the same reference numerals as in the above-cited figures and a description thereof is omitted.

As shown in FIG. 2, the above-described spherical aberration corrector 100 has the octopole field superimposing portion 120. The octopole field superimposing portion 120 superimposes an octopole field on a hexapole field. The deflection portion 130 deflects the electron beam, thus correcting induced four-fold astigmatism. Thus, deviation of the circularity of a diffraction pattern is corrected.

In contrast, as shown in FIG. 16, the spherical aberration corrector 500 has a deflecting field superimposing portion 510, which operates to superimpose a deflecting field on a hexapole field. The deflection portion 130 deflects the electron beam, correcting induced star aberration. Deviation of the circularity of a diffraction pattern is corrected.

The deflecting field superimposing portion 510 superimposes a deflecting field on the hexapole field produced by the hexapole field generating portion 110 to correct deviation of the circularity of a diffraction pattern. In the illustrated example, the deflecting field superimposing portion 510 superimposes a deflecting field on the hexapole field produced by the second multipole element 114. The deflecting field superimposing portion 510 produces a deflecting field corresponding to the deviation of the circularity of the diffraction pattern. As a result, star aberration is induced.

The deflecting field superimposing portion 510 produces the deflecting field, for example, using a dodecapole field. In the illustrated example, the deflecting field superimposing portion 510 is configured including the second multipole element 114. The deflecting field superimposing portion 510 produces the deflecting field by the use of the second multipole element 114.

Figure 17:
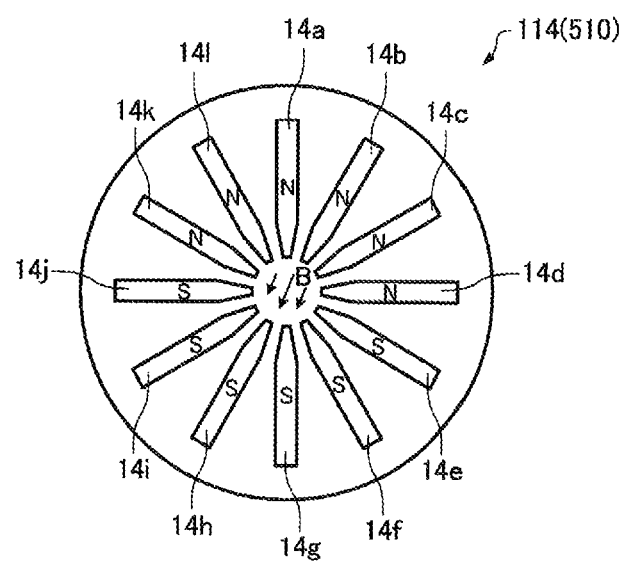
FIG. 17 shows one example of arrangement of magnetic poles of a second multipole element for producing a deflecting field.

FIG. 17 shows one example of arrangement of magnetic poles of the second multipole element 114 for producing the deflecting field.

As shown in FIG. 17, the deflecting field superimposing portion 510 produces the deflecting field by supplying given excitation currents to excitation coils (not shown) mounted on the magnetic poles 14*a*-14*l* of the second multipole element 114. The second multipole element 114 produces the deflecting field by creating two magnetic poles arranged symmetrically with respect to the optical axis A.

The second multipole element 114 produces the hexapole and deflecting fields as described previously. For this purpose, the excitation coils for producing the hexapole field and excitation coils for producing the deflecting field are mounted on the magnetic poles 14*a*-14*l* of the second multipole element 114. The second multipole element 114 produces the hexapole and deflecting fields by supplying given excitation currents to the excitation coils. Thus, superimposed hexapole and deflecting fields can be created. Since the second multipole element 114 is a dodecapole element, the hexapole field (three-fold symmetric field) and deflecting field can be produced by this single multipole element alone.

Figure 18:
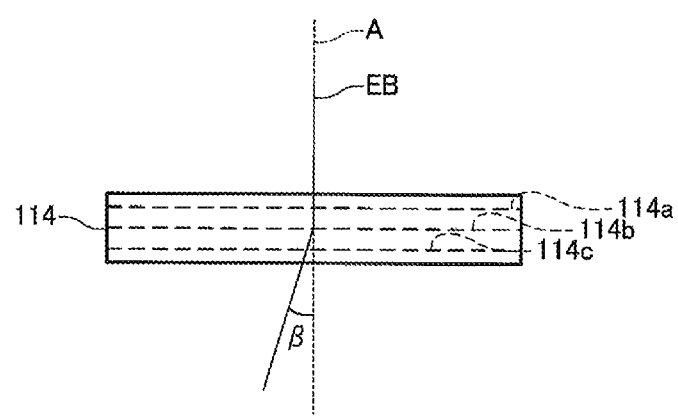
FIG. 18 is a schematic representation of the state of the second multipole element shown in FIG. 17 in which the deflecting field is superimposed on a hexapole field.
Figure 19A:
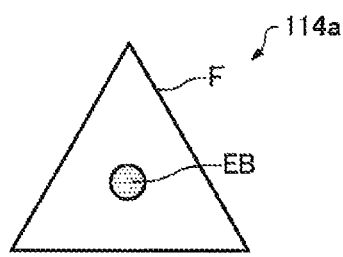
FIG. 19A is a schematic representation of the state of an electron beam on the top surface of the second multipole element shown in FIG. 17.
Figure 19B:
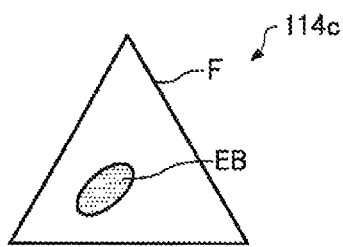
FIG. 19B is a schematic representation similar to FIG. 19A, but showing the state of the electron beam on the bottom surface of the second multipole element.

FIG. 18 schematically shows the state in which the deflecting field is superimposed on the hexapole field in the second multipole element 114. FIG. 19A schematically shows the state of the electron beam EB on the top surface 114*a* of the second multipole element 114. FIG. 19B schematically shows the state of the beam EB on the bottom surface 114*c* of the second multipole element 114.

When the deflecting field superimposing portion 510 superimposes the deflecting field on the hexapole field, the electron beam EB is deflected within the hexapole field as shown in FIG. 18. Consequently, a two-fold symmetric field is produced at a plane (bottom surface 114*c* in the illustrated example) different from the central plane 114*b* (equivalent to a reciprocal plane) of the second multipole element 114. This induces two-fold astigmatism on the bottom surface 114*c* as shown in FIG. 19B. At the top surface 114*a* of the second multipole element 114, no axial misalignment occurs. Also, two-fold astigmatism is not induced. In this way, by superimposing the deflecting field on the hexapole field, different two-fold astigmatisms are induced at two planes different from the central plane of the multipole element. Consequently, the circularities of images and diffraction patterns can be varied.

In FIG. 18, the electron beam EB is tilted at a tilt angle of $\beta$ to the optical axis A by deflecting the beam EB within the hexapole field by means of the deflecting field superimposing portion 510. The circularities of images and diffraction patterns vary according to the magnitude of the tilt angle $\beta$.

The deflection portion 130 deflects the electron beam to adjust the tilt angle $\beta$ of the beam within the hexapole field relative to the optical axis A such that star aberration induced by the deflecting field produced by the deflecting field superimposing field 510 is corrected.

The operation of the spherical aberration corrector 500 is next described.

The spherical aberration corrector 500 corrects spherical aberration using two stages of hexapole fields produced by the hexapole field generating portion 110 in the same way as for the above-described spherical aberration corrector 100.

Furthermore, in the spherical aberration corrector 500, on-axis aberrations and deviations of the circularities of diffraction patterns are corrected by the deflecting field superimposing portion 510 and deflection portion 130.

In particular, the deflecting field superimposing portion 510 superimposes a deflecting field on the second multipole element 114 to correct deviation of the circularity of each diffraction pattern. As a result, star correction is induced.

The deflection portion 130 deflects the electron beam to adjust the tilt angle $\beta$ of the beam within the hexapole fields produced by the multipole elements 112 and 114 such that induced star correction is corrected. That is, the deflection portion 130 deflects the beam to tilt the beam within the hexapole fields, thus correcting the star aberration induced by the deflecting field superimposing portion 510.

As a result, given different two-fold astigmatisms are induced at two planes different from the central plane (diffraction plane equivalent to a reciprocal space) of the multipole elements 112 and 114. As a result, the circularity of the diffraction pattern varies, correcting deviation of the circularity of the diffraction pattern.

In this way, in the spherical aberration corrector 500, star aberration induced by generation of the deflecting field by means of the deflecting field superimposing portion 510 is corrected by deflecting the electron beam using the deflection portion 130. As a result, deviation of the circularity of each diffraction pattern is varied. Consequently, deviation of the circularity of the diffraction pattern can be corrected independently of on-axis aberrations.

The spherical aberration corrector 500 has the following features.

The spherical aberration corrector 500 includes a hexapole field generating portion 110 for producing two stages of hexapole fields, a deflecting field superimposing portion 510 for superimposing a deflecting field on the hexapole field produced by the second multipole element 114 to correct deviation of the circularity of the diffraction pattern, and a deflection portion 130 for deflecting the electron beam. Consequently, deviation of the circularity of the diffraction pattern can be corrected independently of on-axis aberrations as described previously. In this way, a correction of on-axis aberrations and a correction of deviation of the circularity of the diffraction pattern can be carried out independently.

In the spherical aberration corrector 500, the deflection portion 130 adjusts the tilt of the electron beam within the hexapole fields produced by the multipole elements 112 and 114 such that star aberration induced by the deflecting field produced by the deflecting field superimposing field 510 is corrected. The star aberration induced by the deflecting field produced by the deflecting field superimposing portion 510 is corrected because the electron beam is tilted by the deflection portion 130. As a result, deviation of the circularity of the diffraction pattern can be corrected. Accordingly, a correction of on-axis aberrations and a correction of deviation of the circularity of the diffraction pattern can be carried out independently.

3.2. Method of Spherical Aberration Correction

Figure 20:
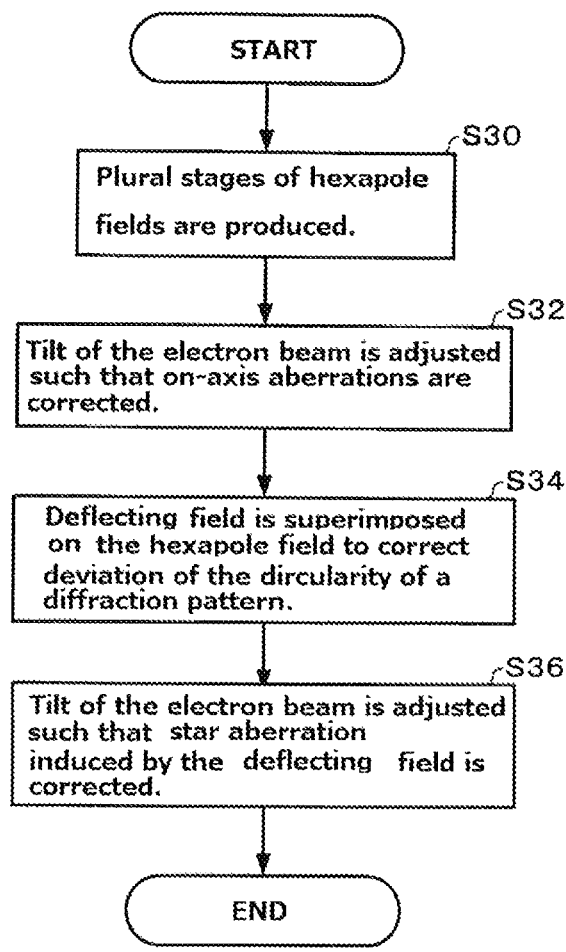
FIG. 20 is a flowchart illustrating one method of spherical aberration correction implemented by a spherical aberration corrector associated with a third embodiment of the invention.

A method of spherical aberration correction implemented by the spherical aberration correction 500 associated with the third embodiment is next described by referring to FIG. 20, which is a flowchart illustrating one example of this method of spherical aberration correction.

First, the hexapole field generating portion 110 produces plural stages of hexapole fields (step S30). This results in a negative spherical aberration, correcting spherical aberration in the objective lens 4.

Then, the deflection portion 130 deflects the electron beam to adjust the tilt of the beam within the hexapole field relative to the optical axis A such that on-axis aberrations are corrected (step S32). Consequently, on-axis aberrations are corrected.

Then, the deflecting field superimposing portion 510 superimposes a deflecting field on the hexapole field produced by the second multipole element 114 to correct deviation of the circularity of the diffraction pattern (step S34). The superimposing portion 510 produces the deflecting field corresponding to the magnitude of the deviation of the circularity of the diffraction pattern. As a result, star aberration is induced.

The deflection portion 130 then deflects the electron beam to adjust the tilt of the electron beam relative to the optical axis A within the hexapole field produced by the hexapole field generating portion 110 such that star aberration induced by the deflecting field produced by the deflecting field superimposing portion 510 is corrected (S36). As a result, the star aberration induced by the deflecting field produced by the deflecting field superimposing portion 510 is canceled out. Deviation of the circularity of the diffraction pattern is corrected.

No restriction is placed on the order in which the steps S32, S34, and S36 are performed.

Spherical aberration can be corrected by the processing steps described so far.

The method of spherical aberration correction implemented by the spherical aberration corrector 500 associated with the third embodiment involves the step S34 for superimposing a deflecting field on one of two stages of hexapole fields to correct deviation of the circularity of each diffraction pattern and the step S36 for adjusting the tilt of the beam within the hexapole field by tilting the beam such that star aberration induced by the deflecting field is corrected. Consequently, a correction of on-axis aberrations and a correction of deviation of the circularity of the diffraction pattern can be carried out independently.

3.3. Modification

Figure 21:
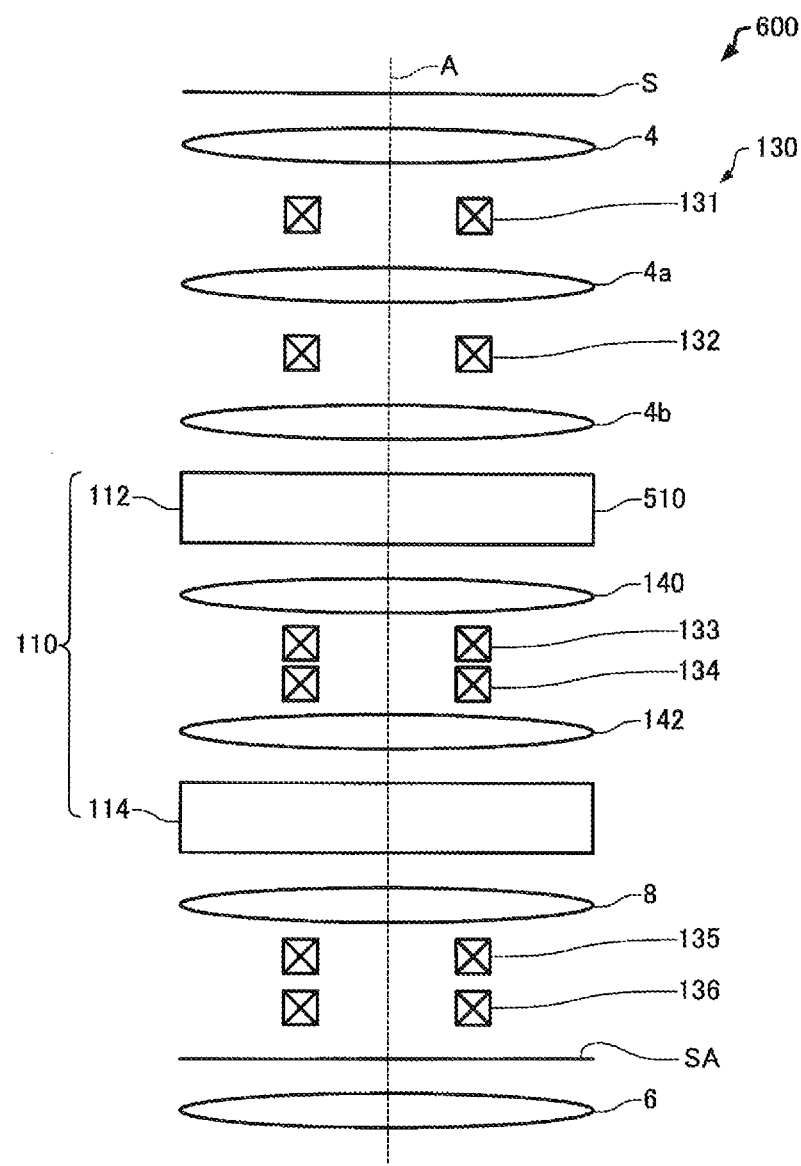
FIG. 21 is a schematic diagram of an optical system for use in a spherical aberration corrector associated with a modification of the third embodiment.

A modification of the third embodiment is next described by referring to FIG. 21, which shows the optical system of a spherical aberration corrector, 600, associated with this modification.

Those components of the spherical aberration corrector 600 associated with the modification of the third embodiment which are similar in function with their respective counterparts of the spherical aberration corrector 500 associated with the third embodiment are indicated by the same reference numerals as in the above-cited figures and a description thereof is omitted.

As shown in FIG. 16, in the above-described spherical aberration corrector 500, the deflecting field superimposing portion 510 is configured including the second multipole element 114, which in turn produces superimposed hexapole and deflecting fields.

In contrast, in the spherical aberration corrector 600, the deflecting field superimposing portion 510 is configured including the first multipole element 112 as shown in FIG. 21. The first multipole element 112 produces superimposed hexapole and deflecting fields.

The spherical aberration corrector 600 yields the same advantageous effects as the spherical aberration corrector 500.

4. Fourth Embodiment

Figure 22:
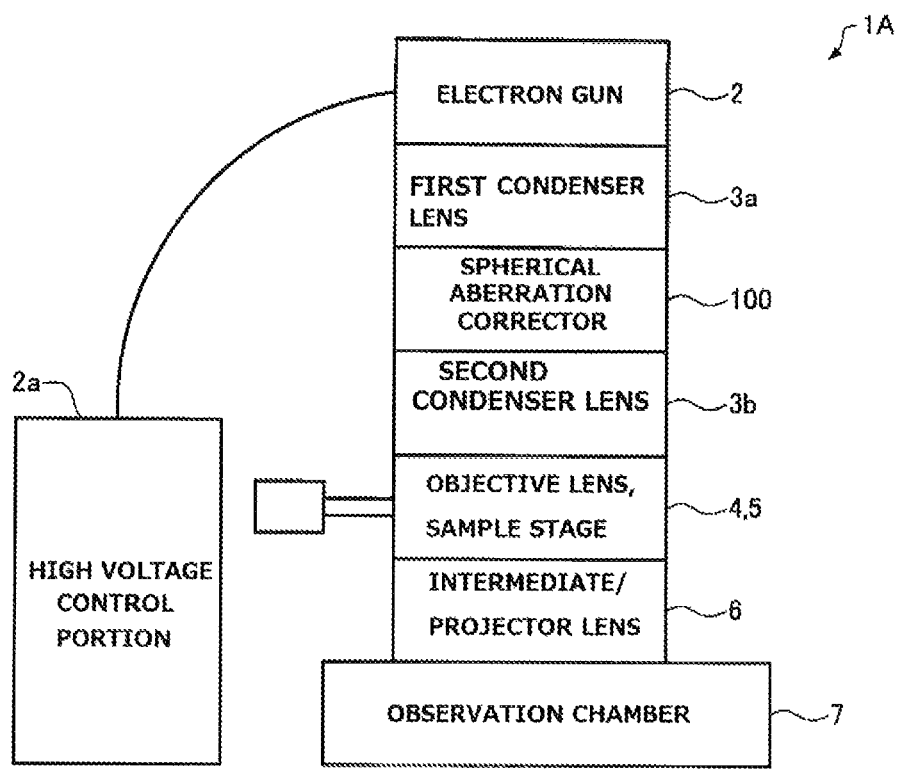
FIG. 22 is a block diagram of a charged particle beam instrument associated with a fourth embodiment of the invention.
Figure 23:
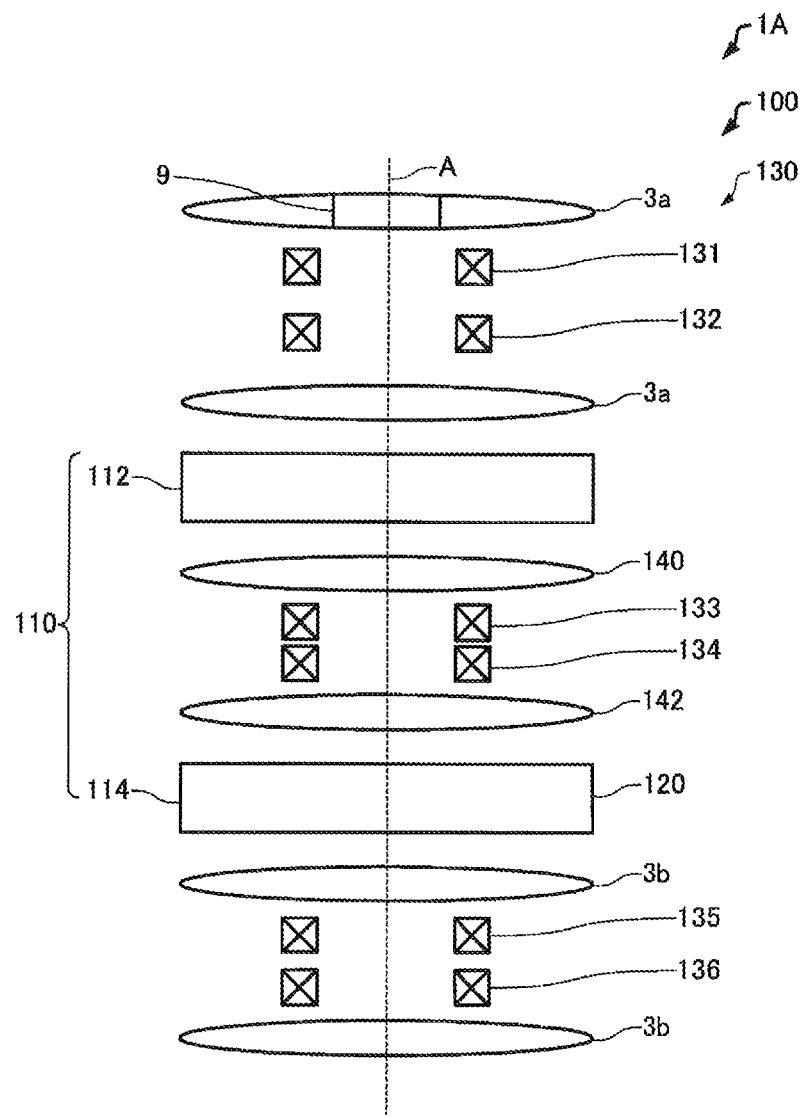
FIG. 23 is a schematic diagram of one example of optical system for use in a spherical aberration corrector that is used with the charged particle beam instrument shown in FIG. 22.

A spherical aberration corrector associated with a fourth embodiment of the invention is next described by referring to FIGS. 22 and 23. FIG. 22 shows the configuration of the charged particle beam instrument, 1A, associated with the fourth embodiment. FIG. 23 shows one example of the optical system of the spherical aberration corrector 100 of the charged particle beam instrument 1A.

Those components of the charged particle beam instrument 1A associated with the fourth embodiment which are similar in function with their respective counterparts of the charged particle beam instrument 1 associated with the first embodiment are indicated by the same reference numerals as in the above-cited figures and a description thereof is omitted.

In the description of the first through third embodiments provided above, the spherical aberration corrector associated with the present invention is used as a spherical aberration corrector for an imaging system.

In contrast, in the charged particle beam instrument 1A associated with the fourth embodiment, the spherical aberration corrector associated with the present invention is used for an illumination system. In the following description, the spherical aberration corrector 100 is used as the spherical aberration corrector associated with the present invention.

As shown in FIGS. 22 and 23, the charged particle beam instrument 1A is configured including an electron gun 2, first condenser lenses 3a, a condenser aperture 9, the spherical aberration corrector 100, a second condenser lens 3b, an objective lens 4, a sample stage 5, an intermediate/projector lens 6, and an observation chamber 7. It is now assumed that the charged particle beam instrument 1A is a scanning transmission electron microscope (STEM).

The condenser aperture 9 is disposed inside and between the first condenser lenses 3a and has a function of cutting out undesired components of the electron beam released from the electron gun 2 and determining the angular aperture and dose of the beam. The condenser aperture 9 has a circularly or otherwise shaped hole.

In the charged particle beam instrument 1A, the electron beam released from the electron gun 2 is focused by the two stages of first condenser lenses 3a and made to enter the spherical aberration corrector 100. In the spherical aberration corrector 100, the aforementioned correction of spherical aberration is made. The electron beam transmitted through the spherical aberration corrector 100 is focused by the second condenser lens 3b and objective lens 4 and made to impinge as an electron probe on the sample. The charged particle beam instrument 1A has scan coils (not shown) which scan the electron probe over the sample. The beam transmitted through the sample is detected by a detector (not shown) inside the observation chamber 7 via the intermediate/projector lens 6. As a consequence, a scanned image and a diffraction pattern are obtained.

In the charged particle beam instrument 1A, deviation of the circularity of the image and on-axis aberration are separately corrected by the spherical aberration corrector 100. In correcting spherical aberration in the illumination system, a deviation of the circularity of the image corresponds to a deviation of the circularity of a shadow of the condenser aperture 9. This shadow can be confirmed in the scanned image.

Where the hole in the condenser aperture 9 is a true circle in shape, if the circularity of the image does not deviate, the shadow of the aperture 9 is observed as a true circle. On the other hand, if the circularity of the image deviates, the shadow of the aperture 9 is observed as a distorted circle.

The operation of the spherical aberration corrector 100 associated with the present embodiment and the method of spherical aberration correction are similar to the corrector and method of the first embodiment except that the octopole field superimposing portion 120 superimposes an octopole field (four-fold symmetric field) on the hexapole field produced by the second multipole element 114 to correct deviation of the circularity of the image (i.e., shadow of the condenser aperture 9) and thus a detailed description of the corrector and method is omitted.

Since the charged particle beam instrument 1A is configured including the spherical aberration corrector 100 permitting a correction of on-axis aberrations and a correction of deviation of the circularity of the image to be carried out independently, good image and diffraction pattern less affected by the effects of spherical aberration, on-axis aberrations, and deviation of the circularity of the image can be obtained.

In the description provided so far, the spherical aberration corrector 100 is applied to the illumination system. The above-described spherical aberration correctors 200, 300, 400, 500, and 600 can be applied with equal utility to the illumination system.

5. Other Embodiments

It is to be understood that the present invention is not restricted to the above embodiments and modifications and that they can be modified variously within the scope and spirit of the invention.

For example, in the description of the spherical aberration correctors 100 to 600 associated with the first through third embodiments and their modifications, a correction of on-axis aberrations and a correction of deviation of the circularity of a diffraction pattern are performed. The spherical aberration correctors 100 to 600 may perform a correction of on-axis aberrations and a correction of deviation of the circularity of a sample image. Where the circularity of the sample image deviates, the sample to be observed as a true circle is observed as a distorted circle.

In particular, in the spherical aberration corrector 100 or 200, the octopole field superimposing portion 120 superimposes a sample image on the hexapole field produced by the second multipole element 114 to correct deviation of the circularity of the image. In the spherical aberration corrector 300 or 400, the quadrupole field superimposing portion 310 superimposes a quadrupole field (four-fold symmetric field) on the hexapole field produced by the second multipole element 114 to correct deviation of the circularity of the sample image. In the spherical aberration corrector 500 or 600, the deflecting field superimposing portion 510 superimposes a deflecting field on the hexapole field produced by the second multipole element 114 to correct deviation of the circularity of the sample image.

The charged particle beam instrument 1 including such a spherical aberration corrector can produce good image and diffraction pattern less affected by the effects of spherical aberration, on-axis aberrations, and deviation of the circularity of the image.

The present invention embraces configurations (e.g., configurations identical in function, method, and results or identical in purpose and advantageous effects) which are substantially identical to the configurations described in any one of the above embodiments. Furthermore, the invention embraces configurations which are similar to the configurations described in any one of the above embodiments except that their nonessential portions have been replaced. Additionally, the invention embraces configurations which are identical in advantageous effects to, or which can achieve the same object as, the configurations described in any one of the above embodiments. Further, the invention embraces configurations which are similar to the configurations described in any one of the above embodiments except that a well-known technique is added.

Having thus described our invention with the detail and particularity required by the Patent Laws, what is desired protected by Letters Patent is set forth in the following claims.

The invention claimed is:

1. A spherical aberration corrector for use with a charged particle beam instrument for obtaining an image and a diffraction pattern, said spherical aberration corrector comprising:
    a hexapole field generating portion for producing plural stages of hexapole fields;
    an octopole field superimposing portion for superimposing an octopole field on at least one of the hexapole fields to correct deviation of the circularity of at least one of the image and diffraction pattern; and
    a deflection portion for deflecting a charged particle beam.

2. The spherical aberration corrector as set forth in claim 1, wherein said deflection portion adjusts a tilt of said charged particle beam within said at least one of said hexapole fields such that four-fold astigmatism induced by said octopole field is corrected.

3. A spherical aberration corrector for use with a charged particle beam instrument for obtaining an image and a diffraction pattern, said spherical aberration corrector comprising:
- a hexapole field generating portion for producing plural stages of hexapole fields;
- a quadrupole field superimposing portion for superimposing a quadrupole field on at least one of the plural stages of hexapole fields to correct deviation of the circularity of at least one of the image and diffraction pattern; and
- a deflection portion for deflecting a charged particle beam.

4. The spherical aberration corrector as set forth in claim 3, wherein said deflection portion adjusts a tilt of said charged particle beam within said at least one of said plural stages of hexapole fields such that star aberration induced by said quadrupole field is corrected.

5. A spherical aberration corrector for use with a charged particle beam instrument for obtaining an image and a diffraction pattern, said spherical aberration corrector comprising:
- a hexapole field generating portion for producing plural stages of hexapole fields;
- a deflecting field superimposing portion for superimposing a deflecting field on at least one of the plural stages of hexapole fields to correct deviation of the circularity of at least one of the image and diffraction pattern; and
- a deflection portion for deflecting a charged particle beam.

6. The spherical aberration corrector as set forth in claim 5, wherein said deflection portion adjusts a tilt of said charged particle beam within said at least one of said plural stages of hexapole fields such that star aberration induced by said deflecting field is corrected.

7. The spherical aberration corrector as set forth in any one of claims 1 to 6, wherein said hexapole field generating portion has two stages of multipole elements.

8. The spherical aberration corrector as set forth in claim 7, further comprising transfer lenses disposed between said two stages of multipole elements.

9. A method of spherical aberration correction implemented in a charged particle beam instrument for obtaining an image and a diffraction pattern, said method comprising the steps of:
- producing plural stages of hexapole fields;
- superimposing an octopole field on at least one of the hexapole fields to correct deviation of the circularity of at least one of said image and diffraction pattern; and
- deflecting a charged particle beam to adjust a tilt of the beam within the at least one of the hexapole fields such that four-fold astigmatism induced by the octopole field is corrected.

10. A method of spherical aberration correction implemented in a charged particle beam instrument for obtaining an image and a diffraction pattern, said method comprising the steps of:
- producing plural stages of hexapole fields;
- superimposing a quadrupole field on at least one of the hexapole fields to correct deviation of the circularity of at least one of said image and diffraction pattern; and
- deflecting a charged particle beam to adjust a tilt of the beam within the at least one of the hexapole fields such that star aberration induced by the quadrupole field is corrected.

11. A method of spherical aberration correction implemented in a charged particle beam instrument for obtaining an image and a diffraction pattern, said method comprising the steps of:
- producing plural stages of hexapole fields;
- superimposing a deflecting field on at least one of the hexapole fields to correct deviation of the circularity of at least one of said image and diffraction pattern; and
- deflecting a charged particle beam to adjust a tilt of the beam within the at least one of the hexapole fields such that star aberration induced by the deflecting field is corrected.

12. The method of spherical aberration correction as set forth in any one of claims 9 to 11, wherein said plural stages of hexapole fields are two stages of hexapole fields.

13. A charged particle beam instrument including a spherical aberration corrector as set forth in any one of claims 1 to 6.

* * * * *